(12) United States Patent
Sherman et al.

(10) Patent No.: US 12,056,208 B2
(45) Date of Patent: Aug. 6, 2024

(54) APPARATUS AND METHOD FOR PERFORMING A LOCALIZATION OF A MOVABLE TREATMENT DEVICE

(71) Applicant: Braun GmbH, Kronberg (DE)

(72) Inventors: Faiz Feisal Sherman, Mason, OH (US); Xiaole Mao, Mason, OH (US)

(73) Assignee: Braun GmbH, Kronberg (DE)

( * ) Notice: Subject to any disclaimer, the term of this patent is extended or adjusted under 35 U.S.C. 154(b) by 1159 days.

(21) Appl. No.: 16/276,993

(22) Filed: Feb. 15, 2019

(65) Prior Publication Data
US 2019/0254795 A1    Aug. 22, 2019

(30) Foreign Application Priority Data

Feb. 19, 2018 (EP) .................................. 18157358
Feb. 19, 2018 (EP) .................................. 18157362

(51) Int. Cl.
*G06F 18/213* (2023.01)
*A46B 15/00* (2006.01)
(Continued)

(52) U.S. Cl.
CPC ........ *G06F 18/213* (2023.01); *A46B 15/0073* (2013.01); *A61C 17/22* (2013.01);
(Continued)

(58) Field of Classification Search
CPC ...... G06F 18/213; G06F 16/285; G06F 18/00; A46B 15/0073; A61C 17/22; A61C 17/16;
(Continued)

(56) References Cited

U.S. PATENT DOCUMENTS 7,835,999 B2    11/2010    Block
7,877,338 B2    1/2011    Tani
(Continued)

FOREIGN PATENT DOCUMENTS

CN    101367015 A    2/2009
CN    102265242 A    11/2011
(Continued)

OTHER PUBLICATIONS

Alex Graves, Abdel-rahman Mohamed and Geoffrey Hinton; "Speech Recognition With Deep Recurrent Neural Networks"; Department of Computer Science, University of Toronto; Mar. 22, 2013.
(Continued)

*Primary Examiner* — Manuel A Rivera Vargas
(74) *Attorney, Agent, or Firm* — Gregory S. Darley-Emerson

(57) ABSTRACT

A method and an apparatus for performing a localization of a movable treatment device having an inertial sensor and configured to treat a target surface. A motion pattern recognition device discriminates between two or more motion patterns contained in a set of motion patterns. An interface provides at least one inertial sensor data from the inertial sensor to the motion pattern recognition device. At least one inertial sensor data represents a movement of the movable treatment device. A neural network is configured to receive the at least one inertial sensor data and to map the at least one inertial sensor data to at least one motion pattern contained in the set of motion patterns associated with one or more different zones of the target surface so that the mapping of the at least one inertial sensor data with the at least one motion pattern indicates an estimation of the location of the device with respect to at least one zone of the target surface.

12 Claims, 12 Drawing Sheets

(51) Int. Cl.
| | |
|---|---|
| A61C 17/22 | (2006.01) |
| A61C 17/26 | (2006.01) |
| G06F 16/28 | (2019.01) |
| G06F 18/00 | (2023.01) |
| G06N 3/044 | (2023.01) |
| G06N 3/08 | (2023.01) |
| G06V 40/20 | (2022.01) |
| G08B 21/18 | (2006.01) |
| A61C 17/16 | (2006.01) |
| A61C 17/34 | (2006.01) |
| B26B 21/40 | (2006.01) |

(52) U.S. Cl.
CPC ............ *A61C 17/221* (2013.01); *A61C 17/26* (2013.01); *G06F 16/285* (2019.01); *G06F 18/00* (2023.01); *G06N 3/044* (2023.01); *G06N 3/08* (2013.01); *G06V 40/20* (2022.01); *G08B 21/18* (2013.01); *A46B 15/0002* (2013.01); *A46B 15/0036* (2013.01); *A46B 15/0038* (2013.01); *A46B 15/004* (2013.01); *A46B 15/0071* (2013.01); *A46B 2200/1066* (2013.01); *A61B 2562/0219* (2013.01); *A61B 2562/0247* (2013.01); *A61B 2562/0252* (2013.01); *A61C 17/16* (2013.01); *A61C 17/3409* (2013.01); *B26B 21/4056* (2013.01); *B26B 21/4081* (2013.01); *G06F 2218/16* (2023.01)

(58) Field of Classification Search
CPC .......... G06N 3/044; G06N 3/08; G08B 21/18; B26B 21/4056; B26B 21/4081; G06V 40/20; A61B 2562/0219; A61B 2562/0247

See application file for complete search history.

(56) References Cited

U.S. PATENT DOCUMENTS

| | | | |
|---|---|---|---|
| 8,175,840 B2 | 5/2012 | Hwang | |
| 8,251,821 B1 | 8/2012 | Yen et al. | |
| 8,554,707 B2 | 10/2013 | Schäfer | |
| 9,144,476 B2 | 9/2015 | Iwahori | |
| 9,263,036 B1 | 2/2016 | Graves | |
| 9,292,102 B2 | 3/2016 | Nasiri et al. | |
| 9,646,244 B2 | 5/2017 | Corrado | |
| 9,820,233 B2 | 11/2017 | Pakzad et al. | |
| 11,755,686 B2 | 9/2023 | Sherman | |
| 2003/0036835 A1 | 2/2003 | Breed et al. | |
| 2005/0219213 A1* | 10/2005 | Cho ...................... | G06F 3/0346 345/158 |
| 2008/0077326 A1 | 3/2008 | Funk et al. | |
| 2008/0102953 A1 | 5/2008 | Schultz | |
| 2008/0174550 A1 | 7/2008 | Laurila et al. | |
| 2009/0092955 A1 | 4/2009 | Hwang | |
| 2010/0145654 A1 | 6/2010 | Hwang | |
| 2011/0010875 A1* | 1/2011 | Iwahori ................... | A46B 13/02 15/22.1 |
| 2011/0060706 A1 | 3/2011 | Suzuki | |
| 2014/0065588 A1* | 3/2014 | Jacobson ............ | A61C 17/225 15/22.1 |
| 2014/0349256 A1 | 11/2014 | Connor | |
| 2015/0109202 A1 | 4/2015 | Ataee et al. | |
| 2015/0189008 A1 | 7/2015 | Krkkinen et al. | |
| 2015/0316383 A1* | 11/2015 | Donikian ............. | G01C 21/165 701/408 |
| 2016/0073886 A1 | 3/2016 | Connor | |
| 2016/0091308 A1 | 3/2016 | Oliaei | |
| 2016/0091965 A1 | 3/2016 | Wang | |
| 2016/0143718 A1 | 5/2016 | Serval | |
| 2016/0235357 A1 | 8/2016 | Ohmer | |
| 2017/0069083 A1 | 3/2017 | Vetter | |
| 2017/0173262 A1 | 6/2017 | Veltz | |
| 2017/0176213 A1 | 6/2017 | Eriksson | |
| 2017/0281054 A1 | 10/2017 | Stever et al. | |
| 2017/0318954 A1 | 11/2017 | Nishiura et al. | |
| 2018/0049001 A1 | 2/2018 | Volozh et al. | |
| 2018/0125623 A1 | 5/2018 | Serval et al. | |
| 2018/0168462 A1 | 6/2018 | Pernu | |
| 2018/0250108 A1 | 9/2018 | Tamminga et al. | |
| 2018/0284745 A1 | 10/2018 | Cella et al. | |
| 2019/0005355 A1 | 1/2019 | Joyce et al. | |
| 2019/0083215 A1 | 3/2019 | Serval et al. | |
| 2019/0200746 A1 | 7/2019 | Serval et al. | |
| 2019/0254794 A1 | 8/2019 | Sherman et al. | |
| 2019/0254796 A1 | 8/2019 | Sherman et al. | |
| 2019/0278786 A1 | 9/2019 | Sherman et al. | |
| 2020/0089214 A1 | 3/2020 | Cella et al. | |
| 2020/0320184 A1 | 10/2020 | Nikitidis et al. | |
| 2020/0371491 A1 | 11/2020 | Wong | |
| 2021/0153989 A1 | 5/2021 | Huang et al. | |
| 2023/0211515 A1 | 7/2023 | Blatter | |
| 2023/0342423 A1 | 10/2023 | Sherman et al. | |

FOREIGN PATENT DOCUMENTS

| | | |
|---|---|---|
| CN | 104848861 A | 8/2015 |
| CN | 105832315 A | 8/2016 |
| CN | 106922185 A | 7/2017 |
| CN | 107092894 A | 8/2017 |
| CN | 107153642 A | 9/2017 |
| CN | 107203753 | 9/2017 |
| CN | 109002189 A | 12/2018 |
| CN | 107516102 B | 10/2020 |
| DE | 4218600 A1 | 12/1993 |
| EP | 3336648 A1 | 6/2018 |
| EP | 3528172 A2 | 8/2019 |
| JP | 2002090267 A | 3/2002 |
| JP | 2009240759 A | 10/2009 |
| JP | 2017187850 A | 10/2017 |
| JP | 2021513415 A | 5/2021 |
| KR | 20130057688 * | 6/2013 |
| KR | 20130057688 A | 6/2013 |
| WO | 2010024697 A1 | 3/2010 |
| WO | 2014089119 A1 | 6/2014 |
| WO | 2017042673 A1 | 3/2017 |
| WO | 2017165231 A1 | 9/2017 |
| WO | 2019081937 A1 | 5/2019 |

OTHER PUBLICATIONS

CM4912M European Search Report with written opinion, dated Oct. 4, 2018, 15 pages.

Dzung Tri Nguyen et al: "SwallowNet: Recurrent neural network detects and characterizes eating patterns", 2017 IEEE International Conference on Pervasive Computing and Communications Workshops (PERCOm Workshops), IEEE, Mar. 13, 2017 (Mar. 13, 2017), pp. 401-406, XP033092320,DOI: 10.1109/PERCOMW.2017. 7917596[retrieved on May 2, 2017]* II.B, IV, V *.

Hssayeni Murtadha D et al.: "Automatic assessment of medication states of patients with Parkinson's disease usingwearable sensors", 2016 38th Annual International Conference of the IEEE Engineering in Medicine Andbiology Society (EMBC), IEEE, Aug. 16, 2016 (Aug. 16, 2016), pp. 6082-6085, XP032980553, DOI: 10.1109/ EMBC.2016.7592116[retrieved on Oct. 13, 2016].

Langkvist Martin et al: "A review of unsupervised feature learning and deep learning for time-series modeling", Pattern Recognition Letters, vol. 42, Jun. 1, 2014 (Jun. 1, 2014), pp. 11-24, XP028831931, ISSN: 0167-8655, DOI: 0.1016/J.PATREC.2014.01.008 * 3.5 and Figure 4 *.

Ming Zeng, Le T. Nguyen, Bo Yu, Ole J. Mengshoel, Jiang Zhu, Pang Wu, Joy Zhang; "Convolutional Neural Networks for Human ActivityRecognition using Mobile Sensors"; 2014 6th International Conference on Mobile Computing, Applications and Services (MobiCASE).

Natalia Neverova, Christian Wolf, Griffin Lacey, Lex Fridman, Deepak Chandra, Brandon Barbello, Graham Taylor "Learning Human Identity from Motion Patterns"; Apr. 21, 2016.

(56) References Cited

OTHER PUBLICATIONS

Nicholas D. Lane, Petko Georgiev; "Can Deep Learning Revolutionize Mobile Sensing?" HotMobile'15, Feb. 12-13, 2015, Santa Fe, NM, USA.
Yousaf Saeed et al: "A Sensor-Augmented Golf Club", a Dissertation submitted to the University of Dublin.
All Office Actions, U.S. Appl. No. 16/277,024.
Partial European Search Report and Search Opinion; Application Ser. No. 19157585.1; dated Jul. 9, 2019; 17 pages.
Partial European Search Report and Search Opinion; Application Ser. No. 18157362.7; dated Sep. 10, 2018; 16 pages.
Extended European Search Report and Search Opinion; Application Ser. No. 19157585.1; dated Dec. 10, 2019; 19 pages.
International Search Report and Written Opinion; Application Ser. No. PCT/IB2019/051249; dated Sep. 18, 2019; 21 pages.
International Search Report and Written Opinion; Application Ser. No. PCT/IB2019/051248; dated Sep. 11, 2019; 22 pages.
Maroon, et al., "Smart Toothbrushes: Inertial Measurement Sensors Fusion with Visual Tracking", In Proceedings of European Conference on Computer Vision, Oct. 8, 2016, pp. 480-494.
Gravina, et al., "Multi-sensor fusion in body sensor networks: State-of-the-art and research challenges", In Journal of Information Fusion, vol. 35, May 2017, pp. 68-80.
Young-Jae Lee et al.: "Toothbrushing Region Detection Using Three-Axis Accelerometer and Magnetic Sensor", IEEE Transactions On Biomedical Engineering, IEEE, USA, vol. 59, No. 3, Mar. 1, 2012 (Mar. 1, 2012), pp. 872-881, XP011490011, ISSN: 0018-9294, DOI: 10.1109/TBME.2011.2181369.
All Office Actions; U.S. Appl. No. 16/276,972, filed on Feb. 15, 2019; See Pair.
All Office Actions; U.S. Appl. No. 16/276,947, filed on Feb. 15, 2019; See Pair.
All Office Actions; U.S. Appl. No. 18/215,248, filed on Jun. 28, 2023; See Pair.
Inoue, et al., "Deep Recurrent Neural Network for Mobile Human Activity Recognition with High Throughput", In Repository of arXiv:1611.03607, Nov. 11, 2016, 10 pages.
Khan, et al., "A Triaxial Accelerometer-Based Physical-Activity Recognition via Augmented-Signal Features and a Hierarchical Recognizer", In Journal of IEEE Transactions on Information Technology in Biomedicine, vol. 14, Issue 5, Sep. 2010, pp. 1166-1172.
Marcon Marco et al.: " Smart Toothbrushes: Inertial Measurement Sensors Fusion with Visual Tracking" In Springer International Publishing, Cham, Nov. 3, 2016, pp. 480-494.
Wang, et al., "Human Activity Recognition with User-Free Accelerometers in the Sensor Networks", In Proceedings of the International Conference on Neural Networks and Brain, Oct. 13, 2005, pp. 1212-1217.

* cited by examiner

```
┌─────────────────────────────────────────────────────────────────┐
│  Discriminating between two or more motion patterns             │
│  ($15_1$, $15_2$, $15_3$, ..., $15_n$) contained in a set (15)  │
│  of motion patterns of the movable treatment device (11)        │
└─────────────────────────────────────────────────────────────────┘
                              │
                              ▼                            ) 801
┌─────────────────────────────────────────────────────────────────┐
│  Receiving at least one inertial sensor data ($17_1$) from the  │
│  inertial sensor (13), the at least one inertial sensor data    │
│  ($17_1$) representing a movement of the movable treatment      │
│  device (11)                                                    │
└─────────────────────────────────────────────────────────────────┘
                              │
                              ▼                            ) 802
┌─────────────────────────────────────────────────────────────────┐
│  Receiving and processing by means of a neural network (18)     │
│  the at least one inertial sensor data ($17_1$) and mapping the │
│  at least one inertial sensor data ($17_1$) to at least one     │
│  motion pattern ($15_1$, $15_2$, $15_3$, ..., $15_n$) contained │
│  in the set (15) of motion patterns, wherein said motion        │
│  patterns ($15_1$, $15_2$, $15_3$, ..., $15_n$) contained in    │
│  the set (15) of motion patterns are each associated with one   │
│  or more different zones ($21_1$, $21_2$, $21_3$, ..., $21_n$)  │
│  of the target surface (12) so that the mapping of the at least │
│  one inertial sensor data ($17_1$) with the at least one motion │
│  pattern ($15_1$, $15_2$, $15_3$, ..., $15_n$) indicates an     │
│  estimation of the location of the movable treatment device     │
│  (11) with respect to the one or more zones ($21_1$, $21_2$,    │
│  $21_3$, ..., $21_n$) of the target surface (12)                │
└─────────────────────────────────────────────────────────────────┘
                                                           ) 803
```

Fig. 8

APPARATUS AND METHOD FOR PERFORMING A LOCALIZATION OF A MOVABLE TREATMENT DEVICE

FIELD OF THE INVENTION

Embodiments of the present invention relate to an apparatus for performing a localization of a movable treatment device, a method for performing a localization of a movable treatment device and a computer program for implementing said method for performing a localization of a movable treatment device when being executed on a computer or signal processor.

Further embodiments of the present invention relate to an apparatus for classifying a motion of a movable personal appliance, a method for classifying a motion of a movable personal appliance and a computer program for implementing said method for classifying a motion of a movable personal appliance when being executed on a computer or signal processor

BACKGROUND OF THE INVENTION

Movable treatment devices may be used for treating a surface or the like. For instance, movable treatment devices may concern personal appliances such as a hair brush, a razor, a groomer, a toothbrush, or the like. In these examples, a surface to be treated may be a body or at least a certain portion or zone of said body.

Other examples of movable treatment devices may, for instance, concern household appliances such as a broom, a mop, a scrubbing brush or the like. In these examples, a surface to be treated may be a floor or at least a certain portion or zone of said floor.

In some applications it might be useful to know the current position of the movable treatment device. In some applications it might be useful to additionally or alternatively classify the motions of the movable treatment device, particularly in the case of a personal appliance.

Nowadays, imaging techniques may be used for localizing movable treatment devices with respect to a target surface by means of a camera capturing said target surface, for instance. It may also be known to use sensors, such as GPS sensors or the like, for localizing a movable treatment device. The aforementioned imaging techniques may also be used for imaging a motion of a movable treatment device and to classify said captured motion.

These common devices and methods may work suitably well for coarse localization and classification. However, several drawbacks may exist. For example, GPS sensors may only work sufficiently well in outdoor conditions. The field of view of a camera capturing a target surface may be obstructed, sometimes even by the movable treatment device itself. Furthermore, even if different users are using the movable treatment device, e.g. the personal appliance, the output of the above-mentioned devices and methods will always be the same for each user even though each user may have individual styles and preferences how to use said movable treatment device.

Thus, it would be desirable to provide apparatuses and methods that allow for a precise localization of a movable treatment device and/or a precise classification of motions of a movable treatment device without the above-mentioned drawbacks. Furthermore, it would be desirable to personalize these apparatuses and methods by providing individually trained techniques for different persons.

SUMMARY OF THE INVENTION

In accordance with one aspect, an apparatus for performing a localization of a movable treatment device relative to a target surface is provided, the movable treatment device comprising an inertial sensor and being configured to treat the target surface. The apparatus may comprise a motion pattern recognition device that may be configured to discriminate between two or more motion patterns which are contained in a set of motion patterns of the movable treatment device. The apparatus may further comprise an interface for providing at least one inertial sensor data from the inertial sensor to the motion pattern recognition device, wherein the at least one inertial sensor data represents a movement of the movable treatment device. The motion pattern recognition device may comprise a neural network that is configured to receive the at least one inertial sensor data. The neural network may further be configured to map the at least one inertial sensor data to at least one of the motion patterns that are contained in the set of motion patterns. Said motion patterns may each be associated with one or more different zones of the target surface so that the mapping of the at least one inertial sensor data with the at least one motion pattern indicates an estimation of the location of the movable treatment device with respect to the one or more zones of the target surface.

In accordance with one aspect, a method is provided for performing a localization of a movable treatment device relative to a target surface, the movable treatment device comprising an inertial sensor and being configured to treat the target surface. The method may comprise a step of discriminating between two or more motion patterns that are contained in a set of motion patterns of the movable treatment device. The inventive method may further comprise a step of receiving at least one inertial sensor data from the inertial sensor, wherein the at least one inertial sensor data represents a movement of the movable treatment device. Furthermore, the inventive method may comprise a step of receiving and processing, by means of a neural network, the at least one inertial sensor data and a step of mapping the at least one inertial sensor data to at least one of the motion patterns contained in the set of motion patterns. Said motion patterns that are contained in the set of motion patterns are each associated with one or more different zones of the target surface so that the step of mapping the at least one inertial sensor data with the at least one motion pattern indicates an estimation of the location of the movable treatment device with respect to the one or more zones of the target surface.

In accordance with one aspect, a computer readable digital storage medium is provided having stored thereon a computer program having a program code for performing, when running on a computer, the above-mentioned method for performing a localization of a movable treatment device relative to a target surface.

In accordance with one aspect, an apparatus is provided for classifying a motion of a movable personal appliance comprising an inertial sensor, wherein the apparatus comprises a motion pattern recognition device configured to discriminate between two or more motion patterns contained in a set of motion patterns of the movable personal appliance. The apparatus may comprise an interface that is configured to provide at least one inertial sensor data from the inertial sensor to the motion pattern recognition device, wherein the at least one inertial sensor data represents a motion of the movable personal appliance. The motion pattern recognition device may comprise a neural network that is configured to receive the at least one inertial sensor data and to map the at least one inertial sensor data to at least one of the motion patterns that are contained in the set of motion patterns. The at least one mapped motion pattern is associated with at least one class member of one or more classes so that the at least one class member is selected based on the motion of the movable personal appliance.

In accordance with one aspect, a method is provided for classifying a motion of a movable personal appliance comprising an inertial sensor. The method may comprise a step of discriminating between two or more motion patterns contained in a set of motion patterns of the movable personal appliance. The method may further comprise a step of providing at least one inertial sensor data from the inertial sensor to the motion pattern recognition device, wherein the at least one inertial sensor data represents a motion of the movable personal appliance. The method may further comprise a step of receiving and processing, by means of a neural network, the at least one inertial sensor data and a step of mapping the at least one inertial sensor data to at least one of the motion patterns contained in the set of motion patterns. The at least one mapped motion pattern is associated with at least one class member of at least one class so that the at least one class member is selected based on the motion of the movable personal appliance.

In accordance with one aspect, a computer readable digital storage medium is provided having stored thereon a computer program having a program code for performing, when running on a computer, the above-mentioned method for classifying a motion of a movable personal appliance.

BRIEF DESCRIPTION OF THE DRAWINGS

FIG. 8 shows a block diagram of an inventive method according to an embodiment.

DETAILED DESCRIPTION OF THE INVENTION

Figure 1:
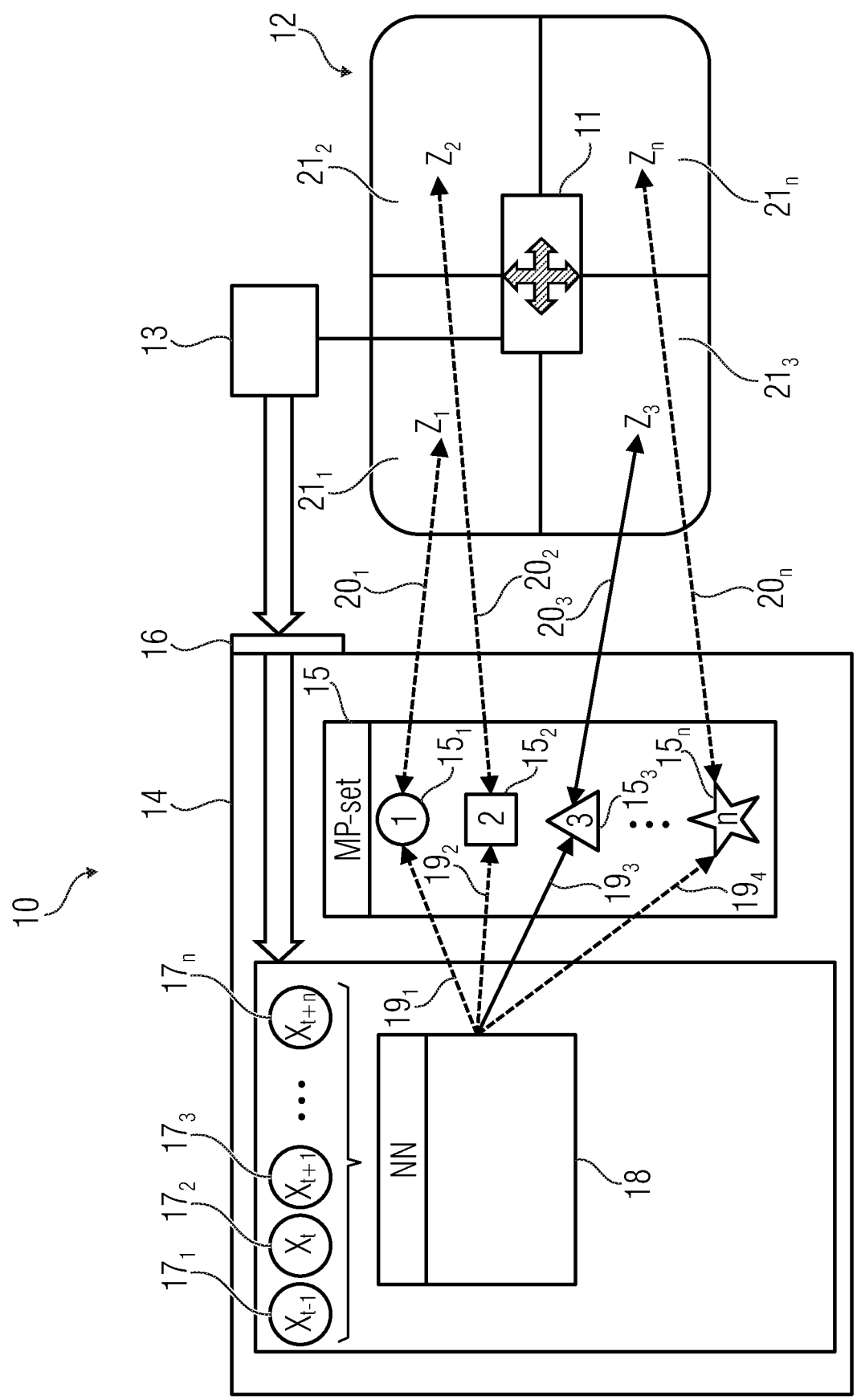
FIG. 1 shows a schematic block diagram of an inventive apparatus according to an embodiment.

Equal or equivalent elements or elements with equal or equivalent functionality are denoted in the following description by equal or equivalent reference numerals.

In the following, reference will and/or household appliances as non-limiting examples for movable treatment devices be made to personal appliances. However, these sorts of appliances are only mentioned as non-limiting examples for the sake of describing embodiments and examples of the present invention. Thus, the invention is not limited to only these exemplarily mentioned sorts of appliances.

Furthermore, an order of any method steps of a method may only be described as a non-limiting example. Accordingly, any method steps as described herein may also be executed in any other order than described.

Although some aspects will be described in the context of an apparatus or device, it is clear that these aspects also represent a description of the corresponding method, where a block or device corresponds to a method step or a feature of a method step. Analogously, aspects described in the context of a method or method step also represent a description of a corresponding block or item or feature of a corresponding apparatus or device.

A first aspect of the present invention concerns an apparatus that is configured to localize a movable treatment device, in particular to localize the movable treatment device with respect to a surface to be treated with said treatment device.

Examples for such movable treatment devices may, for instance, be personal appliances. A personal appliance may be, for instance, a hair brush, a razor, a groomer, a toothbrush, or the like. In these examples, the surface to be treated may be a body or at least a certain portion or zone of said body.

Other examples of movable treatment devices may, for instance, concern household appliances, such as a broom, a mop, a scrubbing brush or the like. In these examples, the surface to be treated may be a floor or at least a certain portion or zone of said floor.

FIG. 1 shows an apparatus 10 according to an embodiment of the present invention. Furthermore, a movable treatment device 11 is depicted. The movable treatment device 11 may comprise an inertial sensor 13. Furthermore, the movable treatment device 11 may be configured to treat a target surface 12.

As can be seen, the movable treatment device 11 may be located at a certain position relative to a target surface 12, for example in, at, on or next to the target surface 12. The target surface 12 itself may be divided into one or more zones $21_1$, $21_2$, $21_3$, ..., $21_n$. The movable treatment device 11 may be moved or be located at a position relative to at least one of said zones $21_1$, $21_2$, $21_3$, ..., $21_n$.

The inventive apparatus 10, as depicted in FIG. 1, is configured to perform a localization of the movable treatment device 11 relative to the target surface 12.

The apparatus 10 may comprise a motion pattern recognition device 14. The motion pattern recognition device 14 may be configured to discriminate between two or more motion patterns $15_1$, $15_2$, $15_3$, ..., $15_n$ that are contained in a set 15 of motion patterns of the movable treatment device 11. In other words, the movable treatment device 11 may be moved, e.g. by a user using said movable treatment device 11, in different linear and/or rotational directions. Accordingly, each motion of the movable treatment device 11 may represent a respective or individual motion pattern. The motion pattern recognition device 14 may comprise a set 15 of different motion patterns. The set 15 of motion patterns may comprise two or more of said aforementioned respective or individual motion patterns $15_1$, $15_2$, $15_3$, ..., $15_n$. The motion pattern recognition device 14 may be configured to discriminate between these two or more motion patterns $15_1, 15_2, 15_3, \ldots, 15_n$. That is, the motion pattern recognition device 14 may be configured to distinguish a first motion pattern $15_1$ from a second motion pattern $15_2$.

The movement of the movable treatment device 11 may be detected by means of the at least one inertial sensor 13 that the movable treatment device 11 comprises. The inertial sensor 13 is a sensor based on inertia and may comprise at least one of an accelerometer, a gyroscope and a magnetometer. The inertial sensor 13 may provide sensor data representing at least one of a linear velocity, an angular velocity, a linear acceleration, an angular acceleration and a g-force. The inertial sensor 13 may be part of an inertial measurement unit comprising one or more inertial sensors.

The apparatus 10 may comprise an interface 16 for receiving at least one inertial sensor data $17_1, 17_2, 17_3, \ldots, 17_n$ from the inertial sensor 13 and for providing the at least one inertial sensor data $17_1, 17_2, 17_3, \ldots, 17_n$ to the motion pattern recognition device 14. The at least one inertial sensor data $17_1, 17_2, 17_3, \ldots, 17_n$ represents a movement of the movable treatment device 11. In other words, when the movable treatment device 11 moves, the inertial sensor 13 senses this motion and creates at least one inertial sensor data $17_1, 17_2, 17_3, \ldots, 17_n$. Accordingly, the at least one inertial sensor data $17_1, 17_2, 17_3, \ldots, 17_n$ represents the respective motion of the moved treatment device 11.

According to the invention, the motion pattern recognition device 14 may comprise a neural network 18. The neural network 18 may be a deep learning network. The neural network 18 may be configured to receive the at least one inertial sensor data $17_1, 17_2, 17_3, \ldots, 17_n$ and to map the at least one inertial sensor data $17_1, 17_2, 17_3, \ldots, 17_n$ to at least one of the motion patterns $15_1, 15_2, 15_3, \ldots, 15_n$ contained in the set 15 of motion patterns. This mapping is indicated in FIG. 1 by means of the dashed and solid arrows $19_1, 19_2, 19_3, 19_4$. The arrow $19_3$ that is drawn in solid lines may exemplarily indicate that the neural network 18 successfully mapped the at least one inertial sensor data $17_1, 17_2, 17_3, \ldots, 17_n$ to the third motion pattern $15_3$.

The different motion patterns $15_1, 15_2, 15_3, \ldots, 15_n$ that are contained in the set 15 are exemplarily symbolized by different geometrical shapes (circle, rectangle, triangle, star) merely for illustration purposes. The motion patterns of the movable treatment device 11 are, of course, not limited to these specific geometrical shapes.

According to the inventive principle, the motion patterns $15_1, 15_2, 15_3, \ldots, 15_n$ are each associated with one or more different zones $21_1, 21_2, 21_3, \ldots, 21_n$ of the target surface 12. This is indicated by means of the dashed and solid arrows $20_1, 20_2, 20_3, \ldots, 20_n$. As can be seen, the first motion pattern $15_1$ may be associated with a first zone $21_1$ of the target surface 12, as is indicated by the dashed arrow $20_1$. The second motion pattern $15_2$ may be associated with a second zone $21_2$ of the target surface 12, as is indicated by the dashed arrow $20_2$. The third motion pattern $15_3$ may be associated with a third zone $21_3$ of the target surface 12, as is indicated by the arrow $20_3$ that is drawn in solid lines. The fourth motion pattern $15_4$ may be associated with a fourth zone $21_4$ of the target surface 12, as is indicated by the dashed arrow $20_4$.

The arrow $20_3$ that is drawn in solid lines may exemplarily indicate that the third motion pattern $15_3$, to which the at least one inertial sensor data $17_1, 17_2, 17_3, \ldots, 17_n$ was successfully mapped by the neural network 18, is associated with the third zone $21_3$ of the target surface 12.

Accordingly, the mapping of the at least one inertial sensor data $17_1, 17_2, 17_3, \ldots, 17_n$ with the at least one motion pattern $15_1, 15_2, 15_3, \ldots, 15_n$ indicates an estimation of the location of the movable treatment device 11 with respect to the one or more zones $21_1, 21_2, 21_3, \ldots, 21_n$ of the target surface 12. In the present example, the mapping of the at least one inertial sensor data $17_1, 17_2, 17_3, \ldots, 17_n$ with the third motion pattern $15_3$ indicates an estimation of the location of the movable treatment device 11 with respect to the third zone $21_3$ of the target surface 12.

In other words, the neural network 18 successfully mapped the received at least one inertial sensor data $17_1, 17_2, 17_3, \ldots, 17_n$ to the third motion pattern $15_3$. Since, according to this example, the third motion pattern $15_3$ is associated with the third zone $21_3$, the apparatus 10 retrieves the information that the movable treatment device 11 is located at the third zone $21_3$, or that the movable treatment device 11 at least was located at the third zone $21_3$ at the time when the at least one inertial sensor data $17_1, 17_2, 17_3, \ldots, 17_n$ was created.

Thus, the apparatus 10 may be configured to localize the movable treatment device 11 relative to the target surface 12 simply by means of the executed motion, or motion pattern, of the movable treatment device 11.

According to an embodiment, the movable treatment device 11 may be a personal appliance and the target surface 12 may be a body portion to be treated by the movable treatment device 11.

For example, the movable treatment device 11 may be a razor or a groomer for shaving or grooming a body portion of a user's body. The user's body may be the target surface 12 in this case. The user's body 12 may be separated into different zones, for instance, a left cheek zone, a right cheek zone, a chin zone and so on. By executing a predetermined motion pattern with the razor 11 the apparatus 10 may localize the razor 11 relative to the user's body. For instance, if the razor 11 executes a motion pattern that is directed into an upper left corner with the razor 11 being tilted to the left, the apparatus 10 may localize the razor 11 as being located in the left cheek zone, for example. Accordingly, the apparatus 10 may localize the razor 11 at the user's face simply by its executed motion pattern.

As a further example, the movable treatment device 11 may be a household appliance and the target surface 12 may be a surface of a floor, a wall, a furniture or the like. For example, the movable treatment device 11 may be a vacuum cleaner and the target surface 12 may be the floor of a room. The room 12 may be separated into different zones, for instance, a left top corner of the room, a right bottom corner of the room, a center of the room, underneath a bed located inside the room, and so on. By executing a predetermined motion pattern with the vacuum cleaner 11 the apparatus 10 may localize the vacuum cleaner 11 relative to the floor of the room. For instance, if the vacuum cleaner 11 executes a motion pattern that is merely directed forwards and backwards with the lance of the vacuum cleaner 11 being lowered near to the ground, the apparatus 10 may localize the vacuum cleaner 11 as being located in the "underneath the bed" zone, for example. Accordingly, the apparatus 10 may localize the vacuum cleaner 11 inside the room simply by its executed motion pattern.

According to a further embodiment, the movable treatment device 11 may be an oral care device and the target surface 12 may be a dentition, wherein the dentition 12 is separated into different dental zones $21_1, 21_2, 21_3, \ldots, 21_n$, wherein the mapping of the at least one inertial sensor data $17_1, 17_2, 17_3, \ldots, 17_n$ with the at least one motion pattern $15_1, 15_2, 15_3, \ldots, 15_n$ indicates an estimation of the location of the oral care device 11 with respect to the one or more dental zones $21_1$, $21_2$, $21_3$, . . . , $21_n$ of the dentition 12.

The oral care device may be a toothbrush, in particular an electric toothbrush. The oral care device may also be at least one of a dental floss, a plaque removing device, an ultrasound device and a waterjet device.

According to this example, by executing a predetermined motion pattern with the oral care device 11 the apparatus 10 may localize the oral care device 11 relative to the dentition. For instance, if the oral care device 11 executes a motion pattern that is merely directed upwards and downwards with the oral care device 11 being tilted to the left, the apparatus 10 may localize the oral care device 11 as being located in a left upper dental zone of the upper jaw, for example. Accordingly, the apparatus 10 may localize the oral care device 11 relative to the user's dentition simply by its executed motion pattern.

According to an embodiment, the dentition may be separated into nine dental zones, wherein a first dental zone corresponds to the left buccal side of the upper and lower jaw of the dentition, a second dental zone corresponds to the occlusal side of the left and right side of the upper jaw of the dentition, a third zone corresponds to the occlusal side of the left and right side of the lower jaw of the dentition, a fourth dental zone corresponds to the left lingual side of the upper and lower jaw of the dentition, a fifth dental zone corresponds to the right buccal side of the upper and lower jaw of the dentition, a sixth dental zone corresponds to the right lingual side of the upper and lower jaw of the dentition, a seventh dental zone corresponds to the labial side of the upper and lower jaw of the dentition, an eighth dental zone corresponds to the palatal side of the upper jaw of the dentition, a ninth dental zone corresponds to the oral side of the front lower jaw of the dentition.

According to a further embodiment, at least one predetermined motion pattern $15_{NB}$ that may be additionally contained in the set 15 of motion patterns may be associated with a zone $21_{NB}$ outside the target surface 12, or not related to the target surface 12, wherein the mapping of the at least one inertial sensor data $17_1$, $17_2$, $17_3$, . . . , $17_n$ with the at least one predetermined motion pattern $15_{NB}$ indicates that the movable treatment device 11 is located in said zone $21_{NB}$ that is outside the target surface 12, or not related to the target surface 12.

In other words, the zone $21_{NB}$ outside the target surface 12 may be a zone that is not directly related to the target surface 12. For example, if the movable treatment device 11 may be a toothbrush, then said zone $21_{NB}$ outside the target surface 12 may be a zone outside the dentition. Accordingly, this zone $21_{NB}$ may indicate that the user is not brushing his teeth. Thus, this zone may also be referred to as a zone 'Not Brushing', abbreviated by 'NB'. This zone $21_{NB}$ may be the at least one zone of the target surface 12, or this zone $21_{NB}$ may be an additional zone in addition to the one or more zones $21_1$, $21_2$, $21_3$, . . . , $21_n$ of the target surface. However, this particular zone $21_{NB}$ outside the target surface 12 is not limited to the above-described example of teeth brushing.

Figure 2:
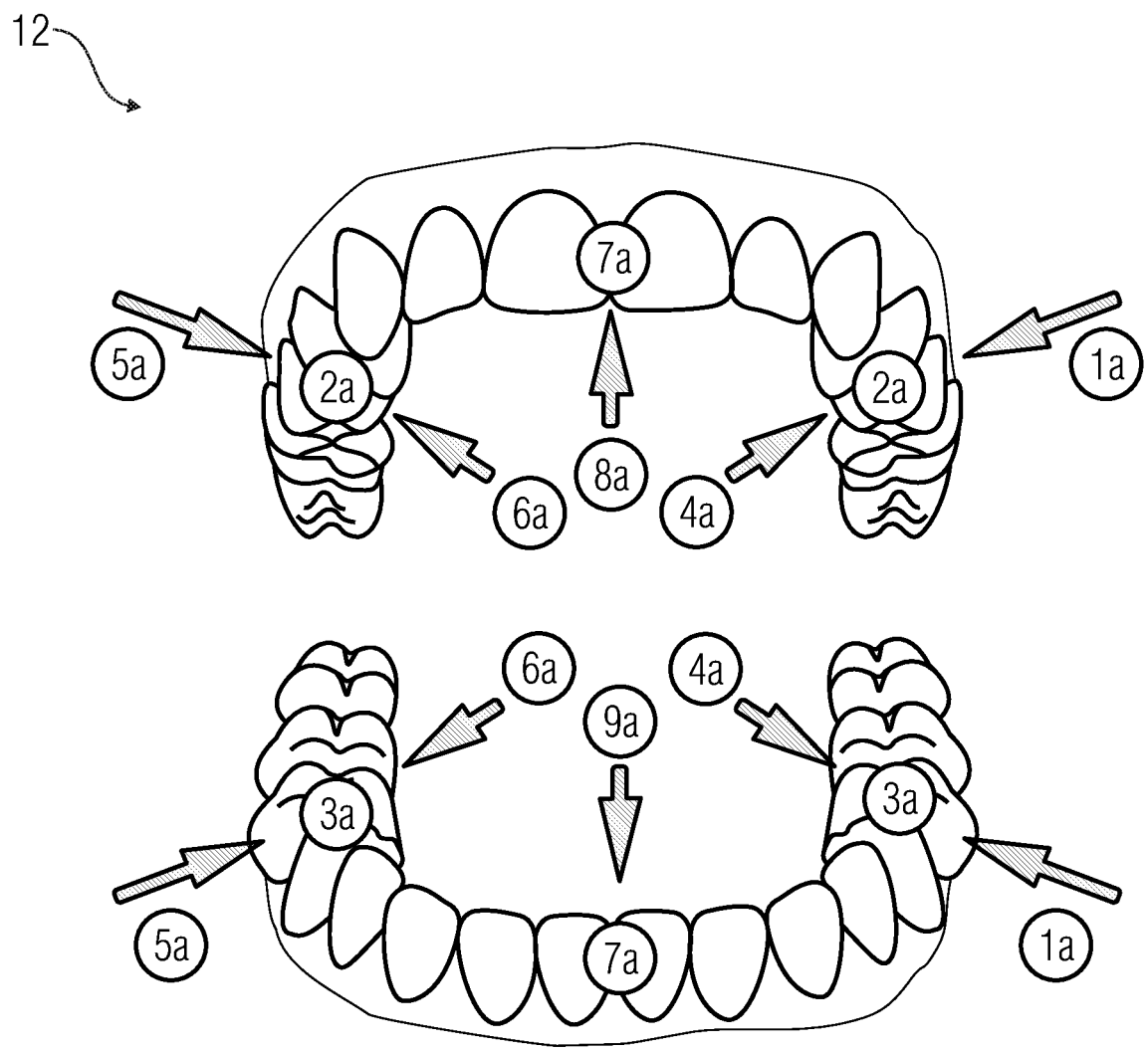
FIG. 2 shows an example of a target surface to be treated with the movable treatment device.

FIG. 2 shows a dentition 12 for illustrating the above-described example. The dentition 12 may be the target surface. The dentition 12 may be separated into nine dental zones 1a to 9a. Optionally, a tenth zone NB may exist. This tenth zone NB is a zone outside the dentition 12. Thus, this tenth zone NB is not explicitly illustrated in FIG. 2. Since this tenth zone NB is not related to one of the dental zones of the dentition 12, and therefore not concerned with brushing the teeth of the dentition 12, this tenth zone NB may also be referred to as a 'Not Brushing' zone.

As can be seen in FIG. 2, a first dental zone 1a may correspond to the left buccal side of the upper and lower jaw of the dentition 12. A second dental zone 2a may correspond to the occlusal side of the left and right side of the upper jaw of the dentition 12. A third zone 3a may correspond to the occlusal side of the left and right side of the lower jaw of the dentition 12. A fourth dental zone 4a may correspond to the left lingual side of the upper and lower jaw of the dentition 12. A fifth dental zone 5a may correspond to the right buccal side of the upper and lower jaw of the dentition 12. A sixth dental zone 6a may correspond to the right lingual side of the upper and lower jaw of the dentition 12. A seventh dental zone 7a may correspond to the labial side of the upper and lower jaw of the dentition 12. An eighth dental zone 8a may correspond to the palatal side of the upper jaw of the dentition 12. A ninth dental zone 9a may correspond to the oral side of the front lower jaw of the dentition 12.

Figure 3:
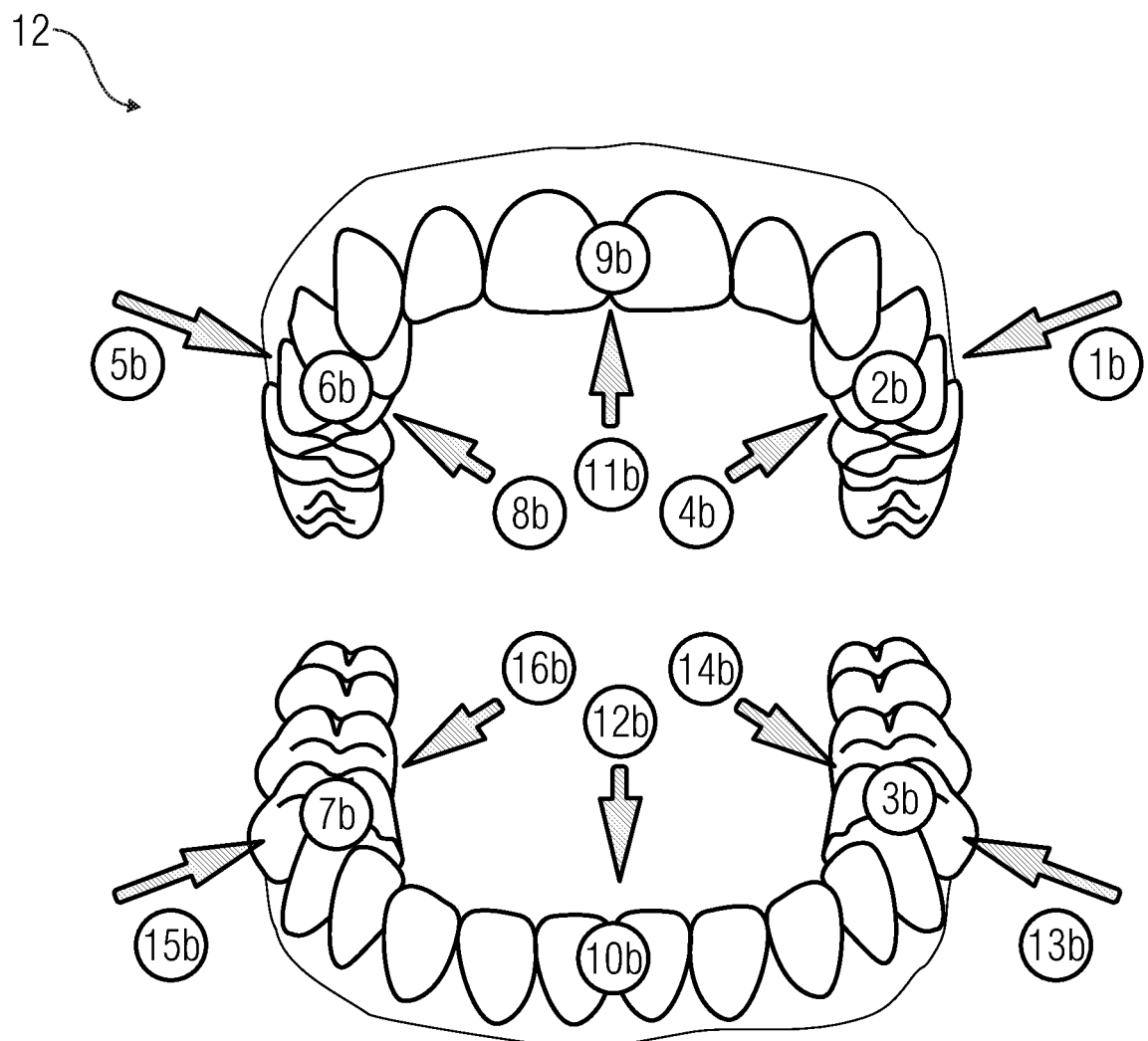
FIG. 3 shows a further example of a target surface to be treated with the movable treatment device.

FIG. 3 shows a dentition 12 for illustrating a further example. The dentition 12 may be the target surface. The dentition 12 may be separated into sixteen dental zones 1b to 16b. Optionally, a seventeenth zone NB may exist. This seventeenth zone NB is a zone outside the dentition 12. Thus, this seventeenth zone NB is not explicitly illustrated in FIG. 3. Since this seventeenth zone NB is not related to one of the dental zones of the dentition 12, and therefore not concerned with brushing the teeth of the dentition 12, this seventeenth zone NB may also be referred to as a 'Not Brushing' zone.

As can be seen in FIG. 3, a first dental zone 1b may correspond to the left buccal side of the upper jaw of the dentition 12. A second dental zone 2b may correspond to the occlusal side of the left side of the upper jaw of the dentition 12. A third dental zone 3b may correspond to the occlusal side of the left side of the lower jaw of the dentition 12. A fourth dental zone 4b may correspond to the left lingual side of the upper and lower jaw of the dentition 12. A fifth dental zone 5b may correspond to the right buccal side of the upper and lower jaw of the dentition 12. A sixth dental zone 6b may correspond to the occlusal side of the right side of the upper jaw of the dentition 12. A seventh dental zone 7b may correspond to the occlusal side of the right side of the lower jaw of the dentition 12. An eighth dental zone 8b may correspond to the palatal side of the upper jaw of the dentition 12. A ninth dental zone 9b may correspond to labial side of the upper jaw of the dentition 12. A tenth dental zone 10b may correspond to the labial side of the lower jaw of the dentition 12. An eleventh dental zone 11b may correspond to the palatal side of the upper jaw of the dentition 12. A twelfth dental zone 12b may correspond to the oral side of the front lower jaw of the dentition 12. A thirteenth dental zone 13b may correspond to the left buccal side of the lower jaw of the dentition 12. A fourteenth dental zone 14b may correspond to the left lingual side of the lower jaw of the dentition 12. A fifteenth dental zone 15b may correspond to the right buccal side of the lower jaw of the dentition 12. A sixteenth dental zone 16b may correspond to the right lingual side of the lower jaw of the dentition 12.

FIGS. 2 and 3 have only been described as non limiting examples. The target surface 12 may also comprise more or less than the exemplarily described nine or sixteen dental zones. Furthermore, the tenth/seventeenth dental zone NB outside the target surface 12 is optional. The exact distribution of the one or more dental zones of the dentition 12 may vary from the examples described above.

One of several advantages of the present invention is the fact that the apparatus 10 is self-learning as regards the localization of the movable treatment device relative to the target surface 12. The apparatus 10 may make use of artificial intelligence, for instance, by exploiting deep learning networks. Accordingly, the apparatus 10 for performing the localization of the movable treatment device 11 relative to the target surface 12 may enhance its performance over time by using the neural network 18.

According to an embodiment, the neural network 18 may be a Recurrent Neural Network (RNN). For example, the neural network may be a Long Short Term Memory (LSTM) network or a Gated Recurrent Unit (GRU) network.

RNNs may suffer from the so-called vanishing gradient problem, wherein gradients vanish quickly with more number of layers. Vanishing gradients may lead to rather slow training rates. Thus, LSTM networks and/or GRU networks may be used to avoid the vanishing gradient problem.

An LSTM network is an artificial neural network containing LSTM blocks in addition to regular network units. An LSTM block contains gates that determine when the input is significant enough to remember, when it should continue to remember or when it should forget the value, and when it should output the value.

Figure 4:
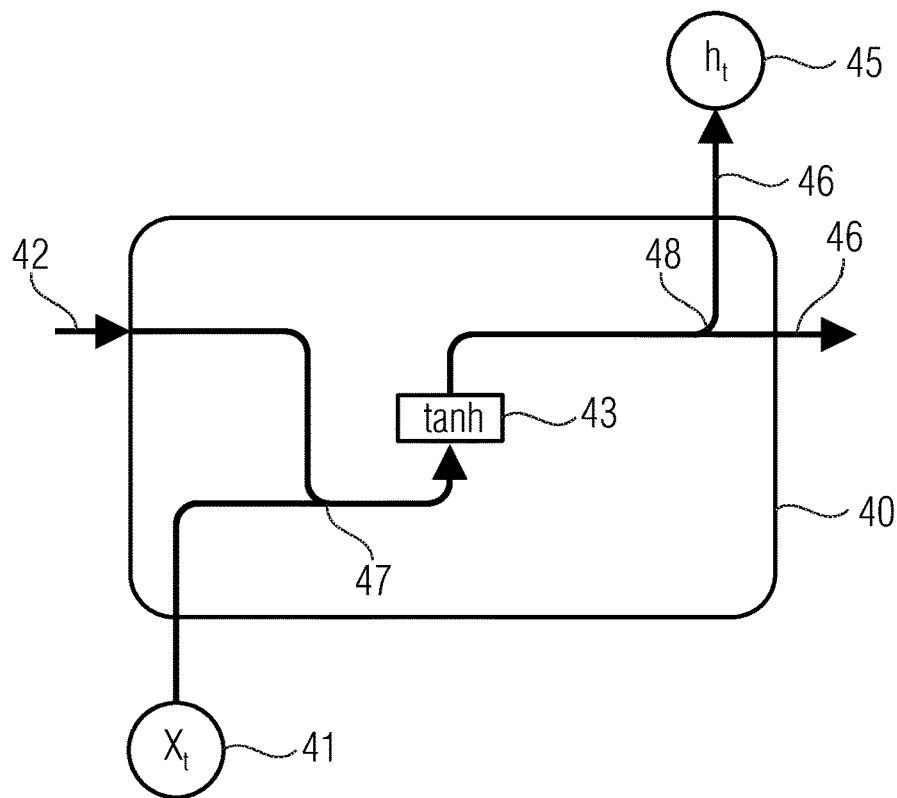
FIG. 4 shows a schematic block diagram of a recurrent neural network that may be used in the inventive apparatus.

FIG. 4 shows an example for a RNN in its most general form. A neural unit 40 may be fed with an input 41 at a certain time instant t. The input 41 may be a single value or a vector comprising two or more values. The input 41 at the certain time instant t may also be symbolized with $X_t$.

The neural unit 40 may optionally also comprise a further input 42. This further input 42 may be provided from a neural unit (not depicted here) at a previous time instant t−1.

The neural unit 40 may comprise at least one gate 43, which may provide a mathematical operation. In this example, the gate 43 is a single tanh gate.

The neural unit 40 may comprise at least one output 46. The output 46 may comprise the result of the operation of the tanh gate 43 that has been fed with the input 41 and optionally the further input 42. The output 46 may lead to a hidden state 45, which will be explained later.

The neural unit 40 may optionally comprise a further output branch 46 which branches off from the above-mentioned output result of the operation of the tanh gate 43 fed with the input 41 and optionally the further input 42.

In FIG. 4, each depicted line may carry an entire vector, from the output of one node to the inputs of others. Lines merging, for instance at 47, denote concatenation, while a line forking, for instance at 48, denote its content being copied and the copies going to different locations. This holds true also for the other neural networks that will be described in the following with reference to the following Figures.

Figure 5:
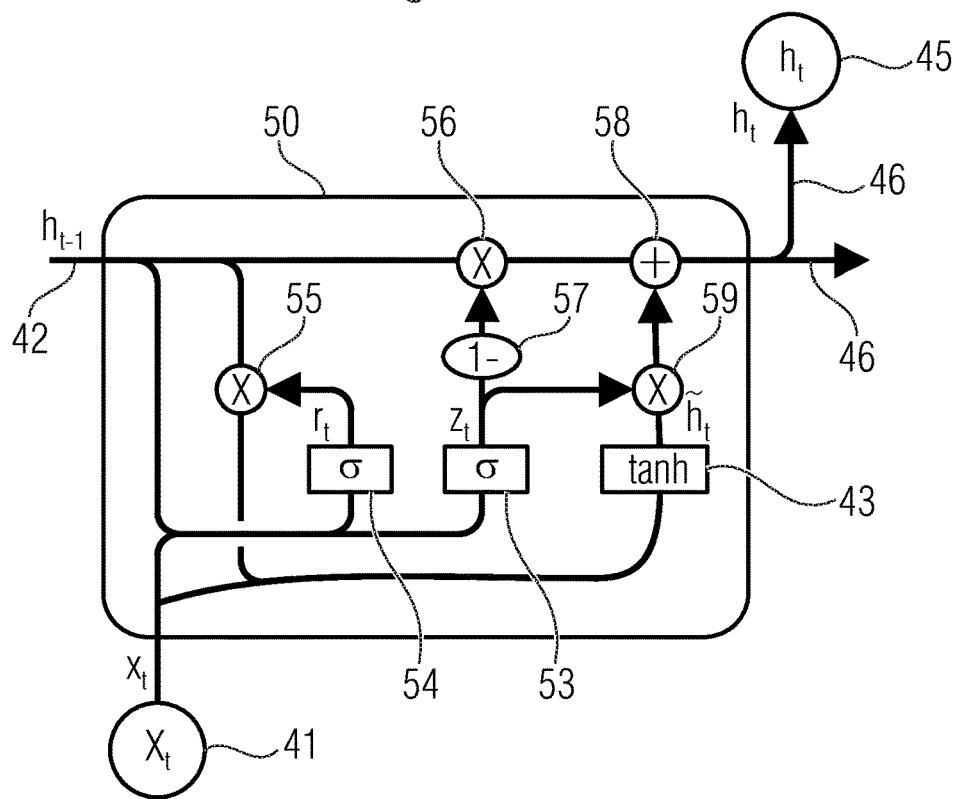
FIG. 5 shows a schematic block diagram of a GRU neural network that may be used in the inventive apparatus.

FIG. 5 shows an example of a GRU network. The GRU network comprises a neural unit 50. In addition to the above-described RNN neural unit 40, the GRU neural unit 50 may comprise two further gates, namely a first sigmoid gate 53 and a second sigmoid gate 54. Furthermore, the GRU neural unit 50 may comprise pointwise operations 55, 56, 57, 58, 59, like vector addition 58, for example.

Figure 6A:
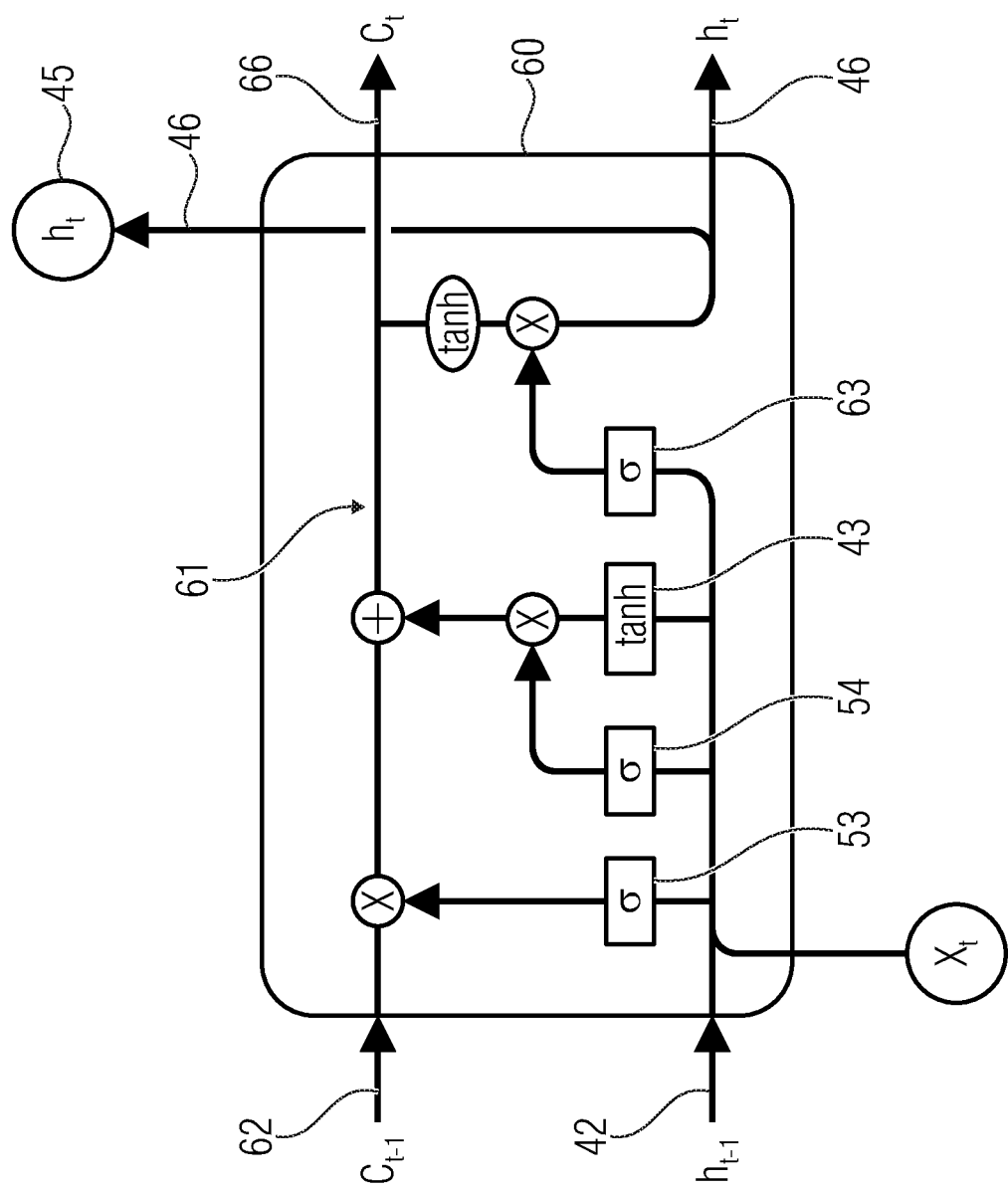
FIG. 6A shows a schematic block diagram of an LSTM neural network that may be used in the inventive apparatus.

FIG. 6A shows an example of an LSTM network that may be exploited as the neural network 18 in the apparatus 10 according to the invention. The LSTM may comprise a neural unit 60 which may, in the case of LSTM networks, also be referred to as an LSTM block. In addition to the above-described neural units 40, 50, the neural unit 60 of the depicted LSTM network may comprise a cell state, which is the horizontal line 61 running through the top of the neural unit 60. The neural unit 60 may receive a cell state input 62 and may create a cell state output 66.

The neural unit 60 may further comprise four gates 43, 53, 54, 63. For example, it may comprise a further sigmoid gate 63 compared to the GRU network described above. Information may be removed or added to the cell state (horizontal line 61) by means of these gates 43, 53, 54, 63.

Figure 6B:
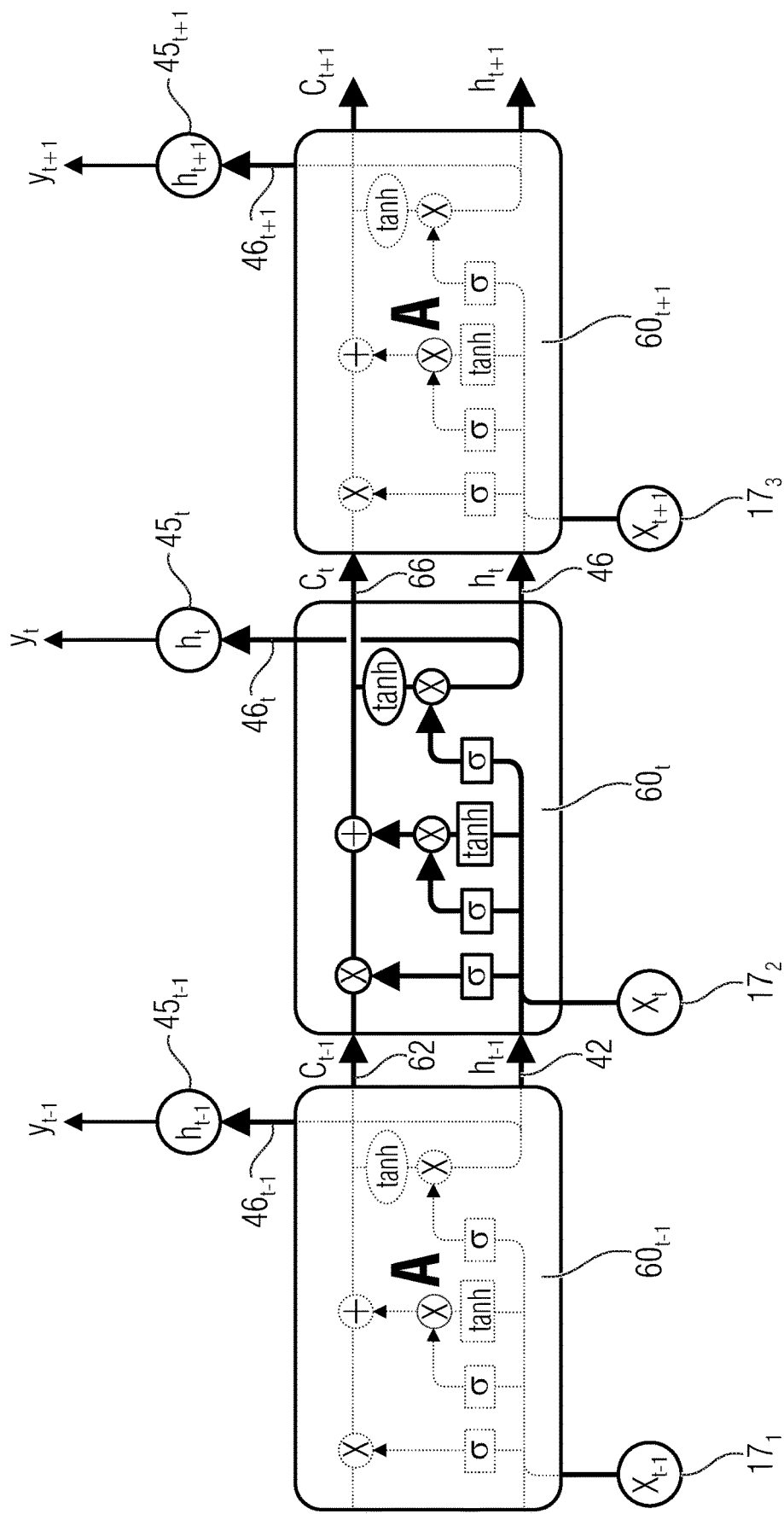
FIG. 6B shows a schematic block diagram of an LSTM neural network with one layer at different time instances.

FIG. 6B shows a further example in which previous and subsequent states (with respect to the time instant t) of the neural unit are depicted. In particular, a neural unit $60_t$ at a time instant t is depicted. Furthermore, a further neural unit $60_{t-1}$ at a previous time instant t−1 is depicted. Still further a further neural unit $60_{t+1}$ at a subsequent time instant t+1 is depicted. The depicted neural units $60_{t-1}$, $60_t$, $60_{t+1}$ may represent the same neural unit but at different points in time, namely at the time instant t, at a previous time instant t−1 and at a subsequent time instant t+1.

The above-described input 41, also symbolized by the letter X, may comprise the at least one sensor data $17_1$, $17_2$, $17_3$, ..., $17_n$ from the inertial sensor 13. The input X may be time dependent, thus X=X(t). In particular, the depicted input $X_t$ may comprise a sensor data $17_2$ acquired during the considered time instant t, the depicted input $X_{t-1}$ may comprise a sensor data $17_1$ acquired during a previous time instant t−1, and the depicted input $X_{t+1}$ may comprise a sensor data $17_3$ acquired during a subsequent time instant t+1.

As can further be seen in FIG. 6B, the neural unit $60_{t-1}$, $60_t$, $60_{t+1}$ may, in each depicted time instant t−1, t, t+1, provide, for instance by prediction, a respective output value $y_{t-1}$, $y_t$, $y_{t+1}$. The output value y(t) may be a single value or a vector comprising one or more vector elements.

The output value y(t) may be calculated as:

$$y_t = \text{softmax}(W_{hy} \cdot h_t + b)$$

The output value y(t) may, for instance, comprise probabilistic values, as will be explained in more detail with respect to FIG. 7. For example, the output value y(t) may be a vector comprising one or more vector elements, wherein each vector element may represent one of the motion patterns $15_1$, $15_2$, $15_3$, ..., $15_n$, or in more detail wherein each vector element may represent a probabilistic value indicating how probable it is that the input X(t), i.e. the inertial sensor data $17_1$, $17_2$, $17_3$, ..., $17_n$, may correspond to one of the motion patterns $15_1$, $15_2$, $15_3$, ..., $15_n$.

Furthermore, the depicted neural units $60_{t-1}$, $60_t$, $60_{t+1}$ may be arranged in the same layer, namely in a first layer. Some examples of the invention may comprise one or more further layers, wherein each layer may comprise its own neural unit(s). Such examples may be described later with reference to FIG. 7 for example. However, examples and embodiments with at least a first layer will be described with further reference to FIG. 6B.

According to this embodiment, the neural network 18 may comprise a first layer, wherein said first layer comprises a neural unit $60_t$, wherein at a first time instant t the at least one inertial sensor data $X_t$ $17_2$ is input into the neural unit $60_t$ of the first layer. At a subsequent second time instant t+1 a second inertial sensor data $X_{t+1}$ $17_3$ and at least one output $h_t$ 46 of the neural unit $60_t$ of the previous first time instant t are input into the neural unit $60_{t+1}$ of the first layer.

Figure 7:
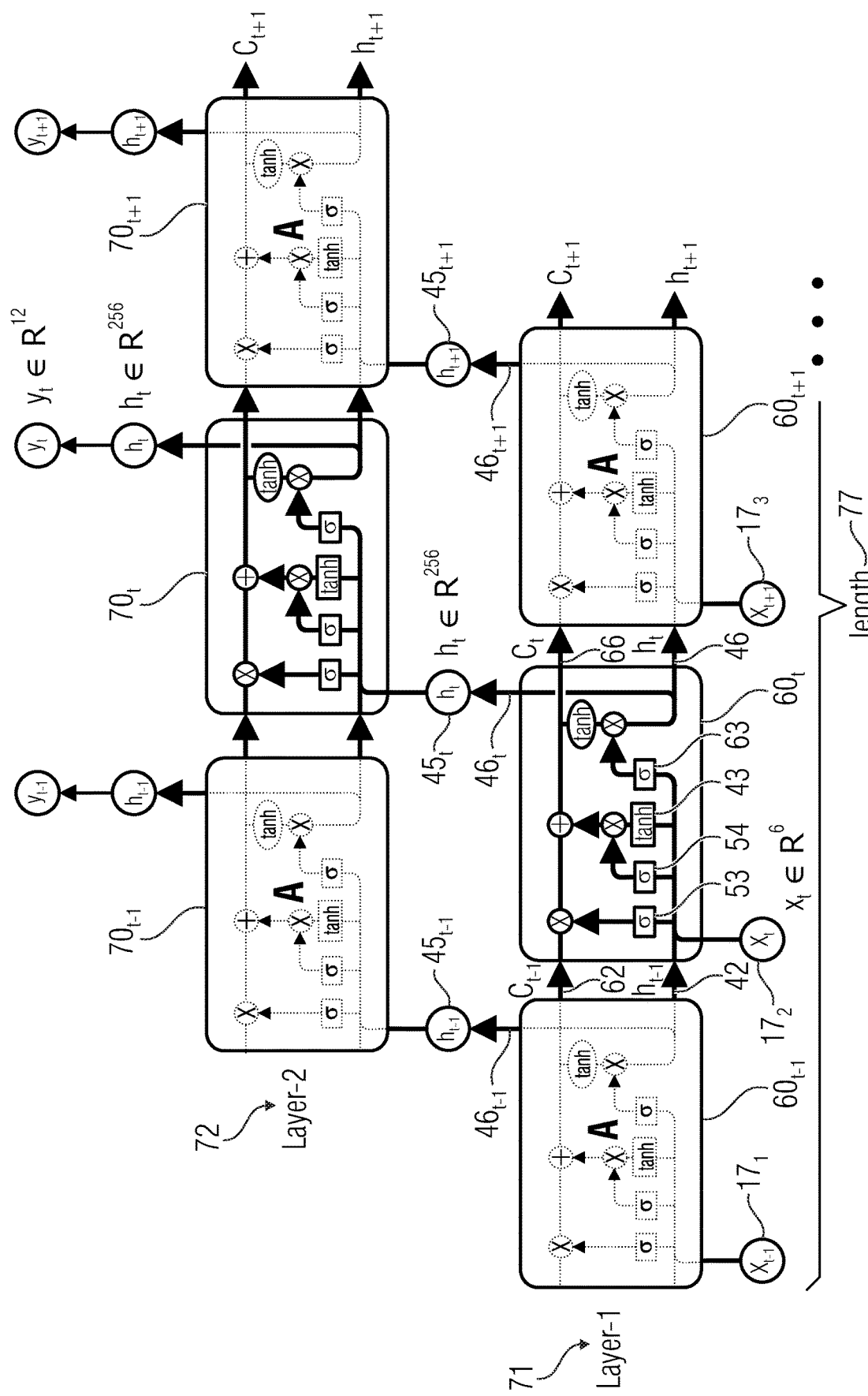
FIG. 7 shows a schematic block diagram of an LSTM neural network with two layers at different time instances.

FIG. 7 shows a further example, wherein the neural network 18 may comprise at least two layers, namely a first layer 71 and a second layer 72. The first layer 71 comprises at least a first neural unit $60_t$, and the second layer 72 comprises at least a second neural unit $70_t$.

As can be seen, the sensor data $17_1$, $17_2$, $17_3$ that is acquired during different time instances t−1, t, t+1 may be fed as input $X_{t-1}$, $X_t$, $X_{t+1}$ into the respective neural unit $60_{t-1}$, $60_t$, $60_{t+1}$ of the first layer 71.

The output $46_{t-1}$, $46_t$, $46_{t+1}$ of each neural unit $60_{t-1}$, $60_t$, $60_{t+1}$ of the first layer 71 may be fed as an input into the respective neural units $70_{t-1}$, $70_t$, $70_{t+1}$ of the second layer 72.

The neural units $60_{t-1}$, $60_t$, $60_{t+1}$ of the first layer 71 and the neural units $70_{t-1}$, $70_t$, $70_{t+1}$ of the second layer 72 may be identical. Alternatively, the internal structure of the neural units $60_{t-1}$, $60_t$, $60_{t+1}$ of the first layer 71 and the neural units $70_{t-1}$, $70_t$, $70_{t+1}$ of the second layer 72 may differ from each other.

According to the embodiment as shown in FIG. 7, the neural network 18 may comprise at least a first layer 71 and a second layer 72, wherein the first layer 71 may comprise a first neural unit $60_t$ and wherein the second layer 72 may comprise a second neural unit $70_t$, wherein at a first time instant t the at least one inertial sensor data $X_t$ $17_2$ is input into the first neural unit $60_t$ of the first layer 71, and wherein an output $h_t$ 46 of the first neural unit $60_t$ is input into the neural unit $70_t$ of the second layer 72.

So far a signal path in a vertical direction, i.e. from a bottom first layer 71 to a top second layer 72 has been described. However, in the embodiment of FIG. 7 also a signal path in a horizontal direction is shown.

As can be seen, the cell state output $C_t$ 66 of a first neural unit $60_t$ at a first time instant t and/or the output $h_t$ 46 of the first neural unit $60_t$ at the first time instant t may be fed as an input into the first neural unit 60 again, namely into the first neural unit $60_{t+1}$ at a subsequent time instant t+1. As already mentioned above, the neural unit 60 itself may be the same neural unit but it may only be depicted in the Figures as a plurality of concatenated neural units $60_{t-1}$, $60_t$, $60_{t+1}$ for ease of illustration of the states of the neural unit 60 at the different time instances t−1, t, t+1. In other words, the horizontal signal path may describe the signal path of the neural unit 60 at different subsequent time instances t−1, t, t+1. The same holds true for the second layer 72 and any further layers.

Accordingly, the depicted subsequent time instances t−1, t, t+1 may represent a length 77 during which the neural network 18 may sample and process the acquired sensor data $17_1$, $17_2$, $17_3$, . . . , $17_n$. Said length 77 may therefore be referred to as a run length, a sample length or a sample period. For example, the sample length 77 may correspond to one second, wherein the time instances t−1, t, t+1 may be fractions of said one second. For example a sample period 77 may have a length of fifty samples, i.e. of fifty time instances. The neural network 18 may run once during a sample period, or the neural network 18 may run permanently over two or more sample periods.

Thus, according to a further embodiment, the neural network 18 may comprise at least a first layer 71 and a second layer 72, wherein the first layer 71 may comprise a first neural unit $60_t$ and wherein the second layer 72 may comprise a second neural unit $70_t$, wherein at a first time instant t the at least one inertial sensor data $X_t$ $17_2$ may be input into the first neural unit $60_t$ of the first layer 71, and wherein at least one output $h_t$ 46 of the first neural unit $60_t$ may be input into the neural unit $70_t$ of the second layer 72. So far it may be the same as described above. However, additionally, at a subsequent second time instant t+1, a second inertial sensor data $X_{t+1}$ $17_3$ and at least one output $h_t$ 46 of the first neural unit $60_t$ at the first time instant t is input into the first neural unit $60_{t+1}$ at the subsequent second time instant t+1.

As mentioned above, several mathematical operations may be executed by the neural network 18, e.g. in the gates 43, 53, 54, 63. In the example shown in FIG. 7 the following mathematical operations may be executed at the different stages:

$$\tilde{h}_j = \sum_{k \in C(j)} h_k,$$
$$i_j = \sigma(W^{(i)} x_j + U^{(i)} \tilde{h}_j + b^{(i)}),$$
$$f_{jk} = \sigma(W^{(f)} x_j + U^{(f)} h_k + b^{(f)}),$$
$$o_j = \sigma(W^{(o)} x_j + U^{(o)} \tilde{h}_j + b^{(o)}),$$
$$u_j = \tanh(W^{(u)} x_j + U^{(u)} \tilde{h}_j + b^{(u)}),$$
$$c_j = i_j \odot u_j + \sum_{k \in C(j)} f_{jk} \odot c_k,$$
$$h_j = o_j \odot \tanh(c_j),$$

wherein
i(t) is the input gate's activation vector;
f(t) is the forget gate's activation vector;
o(t) is the output gate's activation vector;
c(t) is the cell state vector; and
h(t) is the output vector of an LSTM block or neural unit 60, 70.

According to this example, the input sensor data $X_t$ $17_2$ may be an element vector $X_t \in \mathbb{R}^6$. For example it may be an input tensor $X_t \in \mathbb{R}^6$, $[A_x, A_y, A_z, G_x, G_y, G_z]^T$.

Weights W(t) and bias values b(t) are depicted in FIG. 7, wherein in this example:
Weights $W_{hy} \in \mathbb{R}^{12 \times 256}$ and
Bias $b_t \in \mathbb{R}^{12}$.

The output vector y(t) may be calculated as:

$$y_t = \text{softmax}(W_{hy} \cdot h_t + b).$$

The depicted hidden states h(t) may also be element vectors, for example element vectors comprising 256 elements $h_t \in \mathbb{R}^{256}$.

Furthermore, the depicted hidden states C(t) may also be element vectors, for example, element vectors comprising 256 elements $C_t \in \mathbb{R}^{256}$.

As mentioned above, the input inertial sensor data $X_t$ $17_2$ may be an element vector $X_t \in \mathbb{R}^6$ comprising six vector elements, for example an input tensor $X_t \in \mathbb{R}^6$, $[A_x, A_y, A_z, G_x, G_y, G_z]^T$. These vector elements $[A_x, A_y, A_z, G_x, G_y, G_z]^T$ may also be referred to as inertial sensor data portions.

According to an embodiment, the at least one inertial sensor data $17_1$ may comprise at least three inertial sensor data portions of the group comprising a linear velocity in x, y and z direction, an angular velocity with respect to the x, y and z axes, a linear acceleration in x, y and z direction, and an angular acceleration with respect to the x, y and z axes.

In other words, the inertial sensor 13 may provide inertial sensor data $17_1$, $17_2$, $17_3$, . . . , $17_n$ at the one or more time instances t−1, t, t+1, wherein the inertial sensor data $17_1$, $17_2$, $17_3$, . . . , $17_n$ may depend on the current orientation and motion of the movable treatment device 11 at one observed time instance t−1, t, t+1. Each of the inertial sensor data $17_1$, $17_2$, $17_3$, . . . , $17_n$ may be a vector comprising at least three, or in other examples at least six vector elements, wherein said vector elements represent the above-mentioned inertial sensor data portions, wherein at least one of said inertial sensor data portions may be zero.

Accordingly, the inertial sensor data $17_1$, $17_2$, $17_3$, . . . , $17_n$ (vectors), and in particular the sensor data portions (vector elements), may represent the current motion pattern of the movable treatment device 11 as sampled during a sample period 77 comprising one or more subsequent time instances t−1, t, t+1.

According to an embodiment as depicted in FIG. 7, the at least one inertial sensor data $17_2$ (vector) may comprise one or more inertial sensor data portions (vector elements), wherein an input to the neural unit $60_t$ at a first time instant t is a respective inertial sensor data $17_2$ comprising the one or more inertial sensor data portions retrieved during said first time instant t. At least one inertial sensor data $17_1$, $17_2$, $17_3$, . . . , $17n$ may be sampled during a sample time 77.

The neural network 18 may map the at least one sampled inertial sensor data $17_1$, $17_2$, $17_3$, . . . , $17_n$ which has been sampled during the sample time 77 to at least one motion pattern $15_1$, $15_2$, $15_3$, . . . , $15_n$ contained in the set 15 of motion patterns, as it was initially described with reference to FIG. 1. After mapping, the selected one motion pattern may be referred to as a mapped motion pattern.

In other words, the neural network 18 may receive the inertial sensor data $17_1$, $17_2$, $17_3$, . . . , $17_n$ as an input x(t) and it may output one or more probability values as an output y(t). As mentioned above, in the example shown in FIG. 7, the output value y(t) may also be an element vector comprising for example at least three, or at least six, or at least twelve vector elements. Each vector element of the output vector y(t) may represent a probabilistic value for a motion pattern $15_1$, $15_2$, $15_3$, . . . , $15_n$ that may be associated with a class or a zone $21_1$, $21_2$, $21_3$, . . . , $21_n$. In some embodiments, the output value y(t) may be an element vector comprising, for example, at least two to as many needed classes or zones, for example nine zones, twelve zones or sixteen zones.

Accordingly, the output vector y(t) may represent the different zones $21_1$, $21_2$, $21_3$, . . . , $21_n$ of the target surface 12. For example, if the target surface 12 may comprise twelve zones (e.g. eleven dental zones and a twelfth zone 'NB' for not brushing) then the element output vector y(t) may comprise twelve vector elements, such as shown in the example of FIG. 7, wherein $y(t) \in \mathbb{R}^{12}$. Accordingly, each vector element may represent one of the different zones $21_1$, $21_2$, $21_3$, . . . , $21_n$ of the target surface 12.

As mentioned before, the vector elements may represent probability values. These probability values may represent the probabilistic value for each of the different zones $21_1$, $21_2$, $21_3$, . . . , $21_n$ of the target surface 12. In other words, the neural network 18 may receive the at least one inertial sensor data $17_1$, $17_2$, $17_3$, . . . , $17_n$ and map the at least one inertial sensor data $17_1$, $17_2$, $17_3$, . . . , $17_n$ to at least one motion pattern $15_1$, $15_2$, $15_3$, . . . , $15_n$, and since said motion patterns $15_1$, $15_2$, $15_3$, . . . , $15_n$ may each be associated with one or more different zones $21_1$, $21_2$, $21_3$, . . . , $21_n$ of the target surface 12, the probability values may indicate how probable it is, that the acquired at least one inertial sensor data $17_1$, $17_2$, $17_3$, . . . , $17_n$ may correspond to one of the different zones $21_1$, $21_2$, $21_3$, . . . , $21_n$ of the target surface 12.

This is called the mapping of the at least one inertial sensor data $17_1$, $17_2$, $17_3$, . . . , $17_n$ to at least one of the motion patterns $15_1$, $15_2$, $15_3$, . . . , $15_n$.

Since each motion pattern $15_1$, $15_2$, $15_3$, . . . , $15_n$ may be associated with one or more different zones $21_1$, $21_2$, $21_3$, . . . , $21_n$ of the target surface 12, the mapping of the at least one inertial sensor data $17_1$, $17_2$, $17_3$, . . . , $17_n$ with the at least one motion pattern $15_1$, $15_2$, $15_3$, . . . , $15_n$ indicates an estimation of the location of the movable treatment device 11 with respect to the one or more zones $21_1$, $21_2$, $21_3$, . . . , $21_n$ of the target surface 12. The location of the treatment device 11 may be estimated because the inventive location detection may be based on the above-mentioned probability values in contrast to absolute valued geodata from a GPS, for instance.

In other words, the apparatus 10 may derive, from the neural network 18, an estimation in which zone $21_1$, $21_2$, $21_3$, . . . , $21_n$ of the target surface 12 the movable treatment device 11 is located by simply receiving sensor data $17_1$, $17_2$, $17_3$, . . . , $17_n$ and mapping said sensor data $17_1$, $17_2$, $17_3$, . . . , $17_n$ to motion patterns $15_1$, $15_2$, $15_3$, . . . , $15_n$ being associated with one or more zones $21_1$, $21_2$, $21_3$, . . . , $21_n$ of the target surface 12.

Thus, according to an embodiment, an output y(t) of the neural network 18 may comprise one or more probability values for the estimation of the location of the movable treatment device 11 with respect to the one or more zones $21_1$, $21_2$, $21_3$, . . . , $21_n$ of the target surface 12.

According to yet a further embodiment, the motion pattern recognition device 14 may be configured to determine from the at least one inertial sensor data $17_1$, $17_2$, $17_3$, . . . , $17_n$ a mutual movement of the movable treatment device 11 and the target surface 12, and to remove the determined movement of the target surface 12 from the determined movement of the movable treatment device 11.

For example the movable treatment device 11 may be a toothbrush and the target surface 12 may be a user's dentition. The user may turn his head while brushing his teeth. In this case the inertial sensor 13 would sense the mutual movement of the user's head and the toothbrush, since the toothbrush is moved together with the head. This may lead to a wrong motion detection, therefore to a wrong mapping, and finally to a wrong localization based on the mapping.

However, according to the above embodiment the sensed or determined movement of the user's head (target surface) 12 may be removed from the sensed mutual movement of the head and the toothbrush. In result, only the desired movement of the toothbrush (treatment device) 11 remains.

FIG. 8 shows a block diagram of an example of an inventive method for performing a localization of a movable treatment device 11 relative to a target surface 12, wherein the movable treatment device 11 comprises an inertial sensor 13 and wherein the movable treatment device 11 is configured to treat the target surface 12.

In block 801 the method comprises a step of discriminating between two or more motion patterns $15_1$, $15_2$, $15_3$, . . . , $15_n$ contained in a set 15 of motion patterns of the movable treatment device 11.

In block 802 the method comprises a step of receiving at least one inertial sensor data $17_1$, $17_2$, $17_3$, . . . , $17_n$ from the inertial sensor 13, the at least one inertial sensor data $17_1$, $17_2$, $17_3$, . . . , $17_n$ representing a movement of the movable treatment device 11.

In block 803 the method comprises a step of receiving and processing by means of a neural network 18 the at least one inertial sensor data $17_1$, $17_2$, $17_3$, . . . , $17_n$ and mapping the at least one inertial sensor data $17_1$, $17_2$, $17_3$, . . . , $17_n$ to at least one motion pattern $15_1$, $15_2$, $15_3$, . . . , $15_n$ contained in the set 15 of motion patterns, wherein said motion patterns $15_1$, $15_2$, $15_3$, . . . , $15_n$ contained in the set 15 of motion patterns are each associated with one or more different zones $21_1$, $21_2$, $21_3$, . . . , $21_n$ of the target surface 12 so that the mapping of the at least one inertial sensor data $17_1$, $17_2$, $17_3$, . . . , $17_n$ with the at least one motion pattern $15_1$, $15_2$, $15_3$, . . . , $15_n$ indicates an estimation of the location of the movable treatment device 11 with respect to the one or more zones $21_1$, $21_2$, $21_3$, . . . , $21_n$ of the target surface 12.

Figure 9:
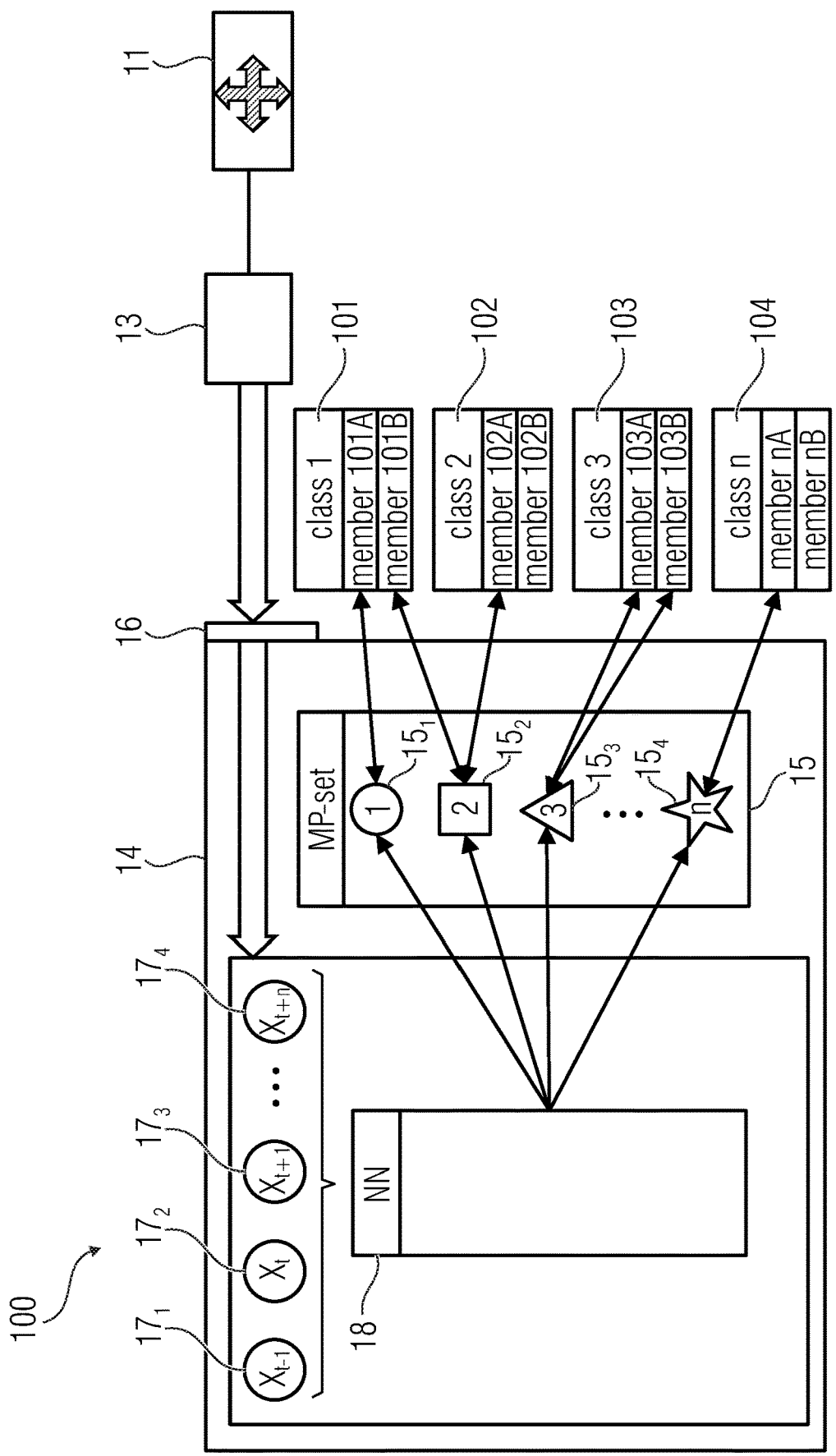
FIG. 9 shows a schematic block diagram of an inventive apparatus according to an embodiment.

FIG. 9 shows an apparatus 100 according to a second aspect of the invention. The apparatus 100 of the second aspect may be similar to the above-described apparatus 10 of the first aspect. Furthermore, all the features described above with respect to the apparatus 10 of the first aspect are combinable with the below described apparatus 100 of the second aspect, and vice versa.

The apparatus 100 of the second aspect may vary from the apparatus 10 of the first aspect (c.f. FIG. 1) in that the motion patterns $15_1$, $15_2$, $15_3$, ..., $15_n$ may be mapped to one or more class members 101A, 101B, ..., 104A, 104B of different classes 101, 102, 103, 104 instead of different zones $21_1$, $21_2$, $21_3$, ..., $21_n$ of a target surface 12.

Accordingly, the apparatus 100 of the second aspect is configured for classifying a motion of a movable personal appliance 11 comprising an inertial sensor 13. The apparatus 100 comprises a motion pattern recognition device 14 configured to discriminate between two or more motion patterns $15_1$, $15_2$, $15_3$, ..., $15_n$ contained in a set 15 of motion patterns of the movable personal appliance 11.

Furthermore, the apparatus 100 comprises an interface 16 for providing at least one inertial sensor data $17_1$, $17_2$, $17_3$, ..., $17_n$ from the inertial sensor 13 to the motion pattern recognition device 14, wherein the at least one inertial sensor data $17_1$, $17_2$, $17_3$, ..., $17_n$ represents a motion of the movable personal appliance 11.

According to the second aspect of the invention, the motion pattern recognition device 14 comprises a neural network 18 that is configured to receive the at least one inertial sensor data $17_1$, $17_2$, $17_3$, ..., $17_n$ and to map the at least one inertial sensor data $17_1$, $17_2$, $17_3$, ..., $17_n$ to at least one motion pattern $15_1$, $15_2$, $15_3$, ..., $15_n$ contained in the set 15 of motion patterns, wherein the at least one mapped motion pattern $15_1$, $15_2$, $15_3$, ..., $15_n$ is associated with at least one class member 101A, 101B, 102A, 102B, 103A, 103B, 104A, 104B of one or more classes 101, 102, 103, 104 so that the at least one class member 101A, 101B, ..., 104A, 104B is selected based on the motion of the movable personal appliance 11.

In other words, the neural network 18 may map the at least one inertial sensor data $17_1$, $17_2$, $17_3$, ..., $17_n$ to at least one motion pattern $15_1$, $15_2$, $15_3$, ..., $15_n$, e.g. in a way as previously described above with reference to FIGS. 1 to 8. Since the mapped motion patterns $15_1$, $15_2$, $15_3$, ..., $15_n$ may each be associated with at least one class member 101A, 101B, ..., 104A, 104B of one or more classes 101, 102, 103, 104, the at least one class member 101A, 101B, ..., 104A, 104B may be selected based on the at least one mapped motion pattern $15_1$, $15_2$, $15_3$, ..., $15_n$ of the movable personal appliance 11, i.e. based on the motion of the movable personal appliance 11.

The non-limiting example of FIG. 9 shows four classes 101, 102, 103, 104, wherein each class comprises two class members 101A, 101B, ..., nA, nB. However, there may be at least one class and each class may comprise at least two class members. There may also be more than two classes or even more than the exemplarily depicted four classes.

As can be seen in the example of FIG. 9, a first mapped motion pattern $15_1$ may be associated with a class member 101A of the first class 101. An $n^{th}$ mapped motion pattern $15_4$ may be associated with a class member nB of the fourth class 104. A second mapped motion pattern $15_2$ may be associated with two class members of different classes, for example with a class member 101B of the first class 101 and with a class member 102A of the second class 102. A third mapped motion pattern $15_3$ may be associated with two class members of the same class, for example with two class members 103A, 103B of the third class.

Generally, at least one mapped motion pattern $15_1$, $15_2$, $15_3$, ..., $15_n$ may be associated with at least one class member 101A, 101B, 102A, 102B, 103A, 103B, 104A, 104B of one or more classes 101, 102, 103, 104.

In the following, some examples of classes and class members will be described.

According to an embodiment, at least one class 101 of the one or more classes 101, 102, 103, 104 may comprise at least one class member 101A, wherein said one class 101 may represent a user group, and wherein said at least one class member 101A may represent at least one user of said user group, wherein the at least one mapped motion pattern $15_1$, $15_2$, $15_3$, ..., $15_n$ may be associated with the at least one class member 101A for identifying said at least one user based on the motion of the movable personal appliance 11.

In other words, one of the classes 101, 102, 103, 104 may represent a user group, i.e. a group of users using the movable personal appliance 11. The respective class may comprise at least one class member that may represent one particular user of said user group. For example, the first class 101 may represent a user group, wherein said user group may be a single household. In this example, the user group 101 may only contain one class member 101A, i.e. one person. The inventive apparatus 100 may be configured to identify said at least one user 101A simply based on the motion of the movable personal appliance 11. Thus, the inventive apparatus 100 may personalize any actions or interactions with said one identified user 101A, as will be described with some examples later.

According to a further embodiment, at least one class 101 of the one or more classes 101, 102, 103, 104 may comprise at least two class members 101A, 101B, wherein said one class 101 may represent a user group, and wherein said at least two class members 101A, 101B may represent at least two users of said user group, wherein the at least one mapped motion pattern $15_1$, $15_2$, $15_3$, ..., $15_n$ may be associated with one of said at least two class members 101A, 101B for identifying at least one user within the user group based on the motion of the movable personal appliance 11.

In other words, one of the classes 101, 102, 103, 104 may represent a user group, i.e. a group of users using the movable personal appliance 11. The respective class may comprise at least one class member that may represent one particular user of said user group. For example, the first class 101 may represent a user group, wherein said user group may be a family. The classes 101A, 101B of said class 101 may represent the family members. For example, the user group 101 may comprise one or more family members, wherein a first class member 101A may represent the mother of the family and a second class member 101B may represent a child of the family, for example.

The inventive apparatus 100 may be configured to identify at least one user simply based on the motion of the movable personal appliance 11. This may be achieved if every user may use the movable personal appliance 11 in a different or individual way.

For example, in an embodiment the movable personal appliance 11 may be a movable oral care device, such as a toothbrush, in particular an electric toothbrush. The movable oral care device may also be at least one of a dental floss, a plaque removing device, an ultrasound device and a waterjet device.

To take up the example above, the mother 101A may use the toothbrush 11 in a different way than the child 101B. The inertial sensor 13 of the toothbrush 11 may provide its inertial sensor data $17_1$, $17_2$, $17_3$, ..., $17_n$ to the motion pattern recognition device 14 comprising the neural network 18. The neural network 18 may map the inertial sensor data $17_1$, $17_2$, $17_3$, ..., $17_n$ to at least one motion pattern $15_1$, $15_2$, $15_3$, ..., $15_n$.

For example, as shown in FIG. 9, the mother may have a brushing style that corresponds to the first motion pattern $15_1$. This motion pattern $15_1$ may be associated with class member 101A that represents the mother. The child instead may have a different brushing style than the mother, for example a brushing style that corresponds to the second motion pattern $15_2$. This motion pattern $15_2$ may be associated with class member 101B that represents the child.

Thus, the inventive apparatus 100 may identify a user of a user group simply based on the motion of the movable personal appliance 11. As mentioned above, the inventive apparatus 100 may personalize any action or interaction with the identified user.

According to an embodiment, the motion pattern recognition device 14 may be configured to select, based on the step of identifying said at least one user 101A, a user-specific motion pattern preset 115 comprising two or more user-specific motion patterns $115_1$, $115_2$, $115_3$, ..., $115_n$ of the movable personal appliance 11 which are characteristic for said identified at least one user 101A.

Figure 10:
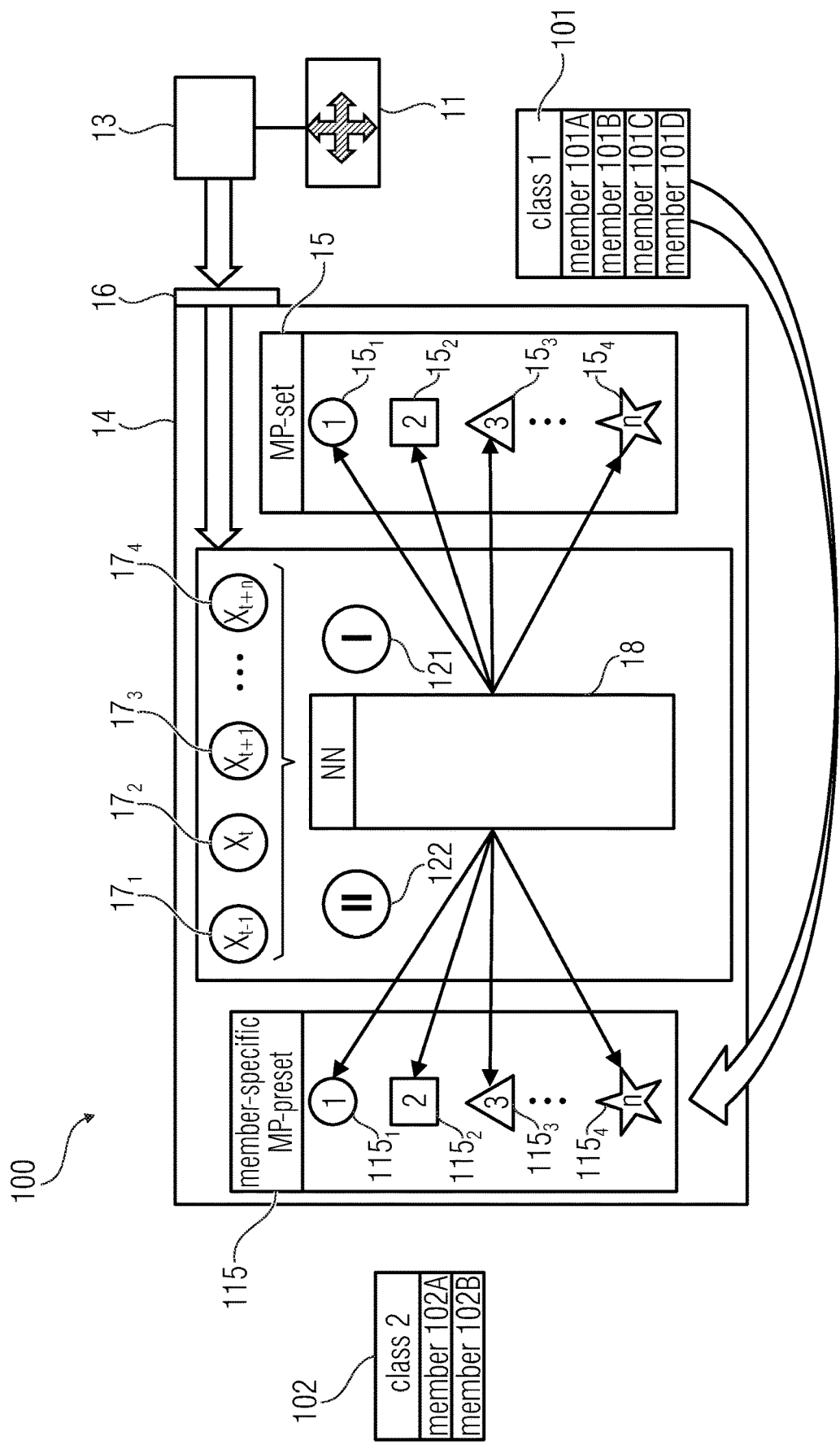
FIG. 10 shows a schematic block diagram of an inventive apparatus according to a further embodiment.

Such an example is shown in FIG. 10. This embodiment may also be referred to as a two-step process. In a first step 121, a user is identified. The identified user may have a user-specific motion pattern preset 115 that has been individually trained by the neural network 18. In a second step 122 the neural network 18 uses the user-specific motion patterns $115_1$, $115_2$, $115_3$, ..., $115_n$ from the user-specific motion pattern preset 115. Thus, the inventive apparatus 100 may act and interact with each identified user individually.

In FIG. 10 a first step 121 is shown in which the neural network 18 receives the at least one inertial sensor data $17_1$, $17_2$, $17_3$, ..., $17_n$ and maps same to at least one of the motion patterns $15_1$, $15_2$, $15_3$, ..., $15_n$ that are contained in the set 15 of motion patterns. The at least one mapped motion pattern, for example the $n_{th}$ notion pattern $15_4$, may be associated with a class member 101B of a first class 101. This procedure may correspond to the procedure as described above with reference to FIG. 9.

The class 101 may be a user group and the class member 101B may be a user of said user group. To take up the above example, the identified user 101B may be the child of the family. The apparatus 100 may have stored user-specific motion patterns. That is, the identified user, i.e. the child 101B, may have its own individual user-specific preset 115 of motion patterns $115_1$, $115_2$, $115_3$, ..., $115_n$ stored in the apparatus 100. For any further actions following the identification in the first step 121, the motion pattern recognition device 14, and in particular the neural network 18, may use these user-specific motion patterns $115_1$, $115_2$, $115_3$, ..., $115_n$ belonging to the previously identified user.

Thus, the neural network 18 may select, after the step 121 of identifying said at least one user 101B, at least one user-specific motion pattern preset 115 comprising two or more user-specific motion patterns $115_1$, $115_2$, $115_3$, ..., $115_n$ of the movable personal appliance 11 which are characteristic for said identified at least one user 101B.

Accordingly, in a second step 122 following the first step 121 of identifying the user, the neural network 18 may use the user-specific preset 115 of user-specific motion patterns $115_1$, $115_2$, $115_3$, ..., $115_n$ in replacement of the set 15 of motion patterns $15_1$, $15_2$, $15_3$, ..., $15_n$. That is, all of the herein described actions that can be executed by the apparatuses 10, 100 by exploiting the set 15 of motion patterns $15_1$, $15_2$, $15_3$, ..., $15_n$ can also be executed individualized or personalized for each identified user by the apparatuses 10, 100 by exploiting the user-specific preset 115 of motion patterns $115_1$, $115_2$, $115_3$, ..., $115_n$ instead of the set 15 of motion patterns $15_1$, $15_2$, $15_3$, ..., $15_n$.

Thus, according to an embodiment the neural network 18 may be configured to replace, after the first step 121 of identifying said at least one user 101B, the set 15 of motion patterns by the selected user-specific motion pattern preset 115, and to replace the two or more motion patterns $15_1$, $15_2$, $15_3$, ..., $15_n$ contained in the set 15 of motion patterns by the two or more user-specific motion patterns $115_1$, $115_2$, $115_3$, ..., $115_n$ contained in the user-specific motion pattern preset 115.

Figure 11:
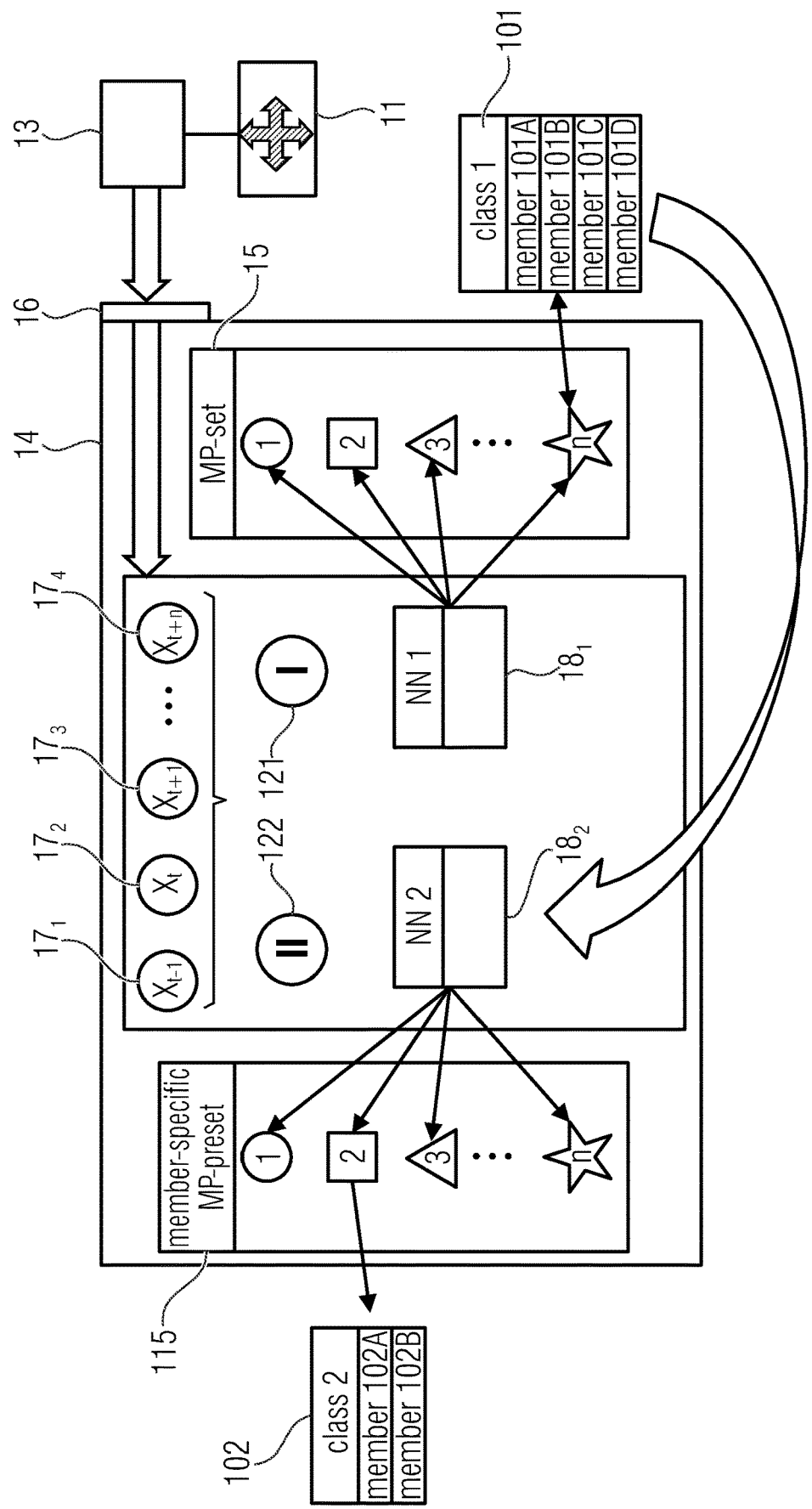
FIG. 11 shows a schematic block diagram of an inventive apparatus according to a further embodiment.

Additionally or alternatively, the apparatus 100 may comprise at least a second neural network. FIG. 11 shows such an example.

The example of the apparatus 100 of FIG. 11 may substantially correspond to the apparatus 100 of the example shown in FIG. 10. The apparatus of FIG. 11 differs from the apparatus of FIG. 10 in that the apparatus of FIG. 11 may comprise a second neural network $18_2$.

As can be seen in FIG. 11, in a first step 121 a first neural network $18_1$ may execute the actions as described above, for example identifying a user 101B of a user group 101. However, in a second step 122, the inertial sensor data $17_1$, $17_2$, $17_3$, ..., $17_n$ may be fed into said second neural network $18_2$. The second neural network $18_2$ may use the user-specific preset 115 of motion patterns $115_1$, $115_2$, $115_3$, ..., $115_n$ as described above.

In other words, after the first step 121 of identifying said at least one user 101B, the motion pattern recognition device 14 may use the second neural network $18_2$, wherein the second neural network $18_2$ may be configured to receive the at least one inertial sensor data $17_1$, $17_2$, $17_3$, ..., $17_n$ and to map the at least one inertial sensor data $17_1$, $17_2$, $17_3$, ..., $17_n$ to at least one user-specific motion pattern $115_1$, $115_2$, $115_3$, ..., $115_n$ contained in the user-specific preset 115 of motion patterns, wherein said user-specific motion patterns $115_1$, $115_2$, $115_3$, ..., $115_n$ are each associated with at least one class member 102A, 102B of one or more classes 101, ..., 104 so that the at least one class member 102A, 102B is selected based on the motion of the movable personal appliance 11. In other words, the neural network 18 may be a user-specifically trained neural network.

Accordingly, the motion pattern recognition device 14 may be configured to use the user-specific preset 115 of user-specific motion patterns $115_1$, $115_2$, $115_3$, ..., $115_n$ for user-specifically classifying the motion of the personal appliance 11 by means of the at least one inertial sensor data $17_1$, $17_2$, $17_3$, ..., $17_n$.

As shown in the examples of FIGS. 10 and 11, the apparatus 100 may comprise at least one class 102 for classifying purposes in the second step 122. However, the apparatus 100 may comprise more than one class, as shown in the example of FIG. 9, in the second step 122.

In said second step 122, for example after having identified a particular user in the first step 121, different actions may be performed by the personal appliance 11. For example, the personal appliance 11 may change its operation mode based on the identified user. For example, the personal appliance 11 may be electrical driven and it may comprise a motor, wherein the personal appliance 11 may change one or more motor specific characteristics, such as frequency, amplitude or pulsation, based on the identified user. Additionally or alternatively, the personal appliance 11 may comprise one or more elements for communicating with or providing feedback to a user, for example a visual element, such as a light, e.g. a LED, or a haptical element, such as a vibrational motor. For example, the personal appliance 11 may change a user experience based on the identified user by changing the operation mode of said elements for communicating, for instance by changing LED lights to a different color or by providing differently pulsed feedback by the vibrational motor, based on the identified user.

Additionally or alternatively, to identifying a particular user of a user group, for example a family member of a family, the apparatus 100 may be configured to identify a particular user type. For example, if the personal appliance 11 was a toothbrush, some people start brushing their teeth with their front teeth or incisors while some other people may start brushing their teeth with their back teeth or molars. In a further example, if the personal appliance was a razor, some people may shave with the grain while some other people may shave against the grain. Summarizing a user type may be a type of user who uses the personal appliance 11 in a particular way. There may be two or more users that can be clustered into groups of user types. The previously described example of user identification instead identifies each user individually.

According to an embodiment for identifying user types, at least one class 104 of the one or more classes 101, 102, 103, 104 may comprise at least two class members nA, nB, wherein said one class 104 may represent a user type of the movable personal appliance 11, wherein a first class member nA may represent a first user type of the movable personal appliance 11 and wherein a second class member nB may represent a second user type of the movable personal appliance 11, wherein the at least one mapped motion pattern $15_1$, $15_2$, $15_3$, ..., $15_n$ may be associated with either the first or the second class member nA, nB for identifying a user type of the movable personal appliance 11 based on the motion of the movable personal appliance 11.

According to a further embodiment, the motion pattern recognition device 14 may be configured to select, after the step of identifying said user type, a user type specific motion pattern preset 115 comprising two or more user type specific motion patterns $115_1$, $115_2$, $115_3$, ..., $115_n$ of the movable personal appliance 11 which are characteristic for said identified user type, and wherein the neural network 18 may be configured to replace, after the step of identifying said user type, the set 15 of motion patterns by the selected user type specific motion pattern preset 115 and to replace the two or more motion patterns $15_1$, $15_2$, $15_3$, ..., $15_n$ contained in the set 15 of motion patterns by the two or more user type specific motion patterns $115_1$, $115_2$, $115_3$, ..., $115_n$.

Everything that has been explained above with respect to the user-specific preset 115 of user-specific motion patterns $115_1$, $115_2$, $115_3$, ..., $115_n$ also holds true for the user type specific preset 115 of user type specific motion patterns $115_1$, $115_2$, $115_3$, ..., $115_n$.

As mentioned above, the identified user types may be clustered into a cluster or group of user types. Therefore, the apparatus 100 may perform a cluster analysis in which a user may use the personal appliance 11 for a predetermined number of times before this user is clustered into a particular user type group. For example, a user may use its razor five times on five subsequent days. On four out of the five days the user may shave against the grain. Thus, after the fifth day the apparatus 100 may cluster this user into a user type group in which all users shaving against the grain are clustered.

The cluster analysis may also be performed at shorter time intervals, i.e. switching the toothbrush 11 on and off may be done directly successively. For example, the user may switch on his electric toothbrush 11 a first time, switch it off, and switch it on a second time to restart the toothbrush 11 again. At the time of restarting the toothbrush 11, the inventive apparatus 100, and in particular the neural network 18, may also be restarted. When the toothbrush 11 is switched on, it may collect information for the cluster analysis. However, at least the neural network 18 shall restart every time before new information for the cluster analysis is collected. Summarizing, the apparatus 100 may repeatedly (e.g. five times) perform the cluster analysis before finally clustering the user into a particular user type group.

After the user has been clustered into a particular user type specific group, the neural network 18 may use the associated user type specific preset 115 of user type specific motion patterns $115_1$, $115_2$, $115_3$, ..., $115_n$.

According to such an embodiment, the motion pattern recognition device 14 may be configured to repeatedly perform a cluster analysis for a predetermined number of times, wherein in each said cluster analysis the neural network 18 may be configured to restart and to perform, after the restart, the step of receiving the at least one inertial sensor data $17_1$, $17_2$, $17_3$, ..., $17_n$ and to map the at least one inertial sensor data $17_1$, $17_2$, $17_3$, ..., $17_n$ to at least one motion pattern $15_1$, $15_2$, $15_3$, ..., $15_n$ contained in the set 15 of motion patterns, and wherein the neural network 18 may be configured to select the user type specific motion pattern preset 115 after performing the cluster analysis for the predetermined number of times.

The inventive apparatus 100 may provide even more scenarios for classifying a motion of the movable personal appliance 11. Therefore, reference shall be made to FIG. 9 again.

According to an embodiment, at least one class 102 of the one or more classes 101, 102, 103, 104 may comprise at least two class members 102A, 102B, wherein said one class 102 may represent a handling evaluation of the movable personal appliance 11, wherein a first class member 102A may represent a correct handling of the movable personal appliance 11 and wherein a second class member 102B may represent a wrong handling of the movable personal appliance 11, wherein the at least one mapped motion pattern $15_1$, $15_2$, $15_3$, ..., $15_n$ may be associated with either the first or the second class member 102A, 102B for evaluating the handling of the movable personal appliance 11 based on the motion of the movable personal appliance 11.

In other words, the apparatus 100 may be configured to check whether a user of the movable personal appliance 11 may use the movable personal appliance 11 correctly or not. Of course, said one class 102 representing the handling evaluation may also be used as a class in the second step 122 of the above-described two-step procedures of FIGS. 10 and 11, e.g. after identifying a user and/or a user type.

According to a further embodiment at least one class 103 of the one or more classes 101, 102, 103, 104 may comprise at least two class members 103A, 103B, wherein said one class 103 may represent a quality of motion execution of the movable personal appliance 11, wherein a first class member 103A may represent a good motion execution of the movable personal appliance 11 and wherein a second class member 103B may represent a bad motion execution of the movable personal appliance 11, wherein the at least one mapped motion pattern $15_1$, $15_2$, $15_3$, ..., $15_n$ may be associated with either the first or the second class member 103A, 103B for evaluating a quality of motion execution of the movable personal appliance 11 based on the motion of the movable personal appliance 11.

In other words, the apparatus 100 may be configured to check whether a user of the movable personal appliance 11 may use the movable personal appliance 11 in a good way or in a bad way. A good way may be a way of performing the motion of the movable personal appliance as intended, while a bad way may be a way of performing the motion of the movable personal appliance 11 as not intended. For example, if the personal appliance 11 was a toothbrush, then the apparatus may check whether the user may have a good or a bad brushing technique.

Of course, said one class 103 representing the quality of motion execution may also be used as a class in the second step 122 of the above-described two-step procedures of FIGS. 10 and 11, e.g. after identifying a user and/or a user type.

Yet a further embodiment of the apparatus 100 may be similar to the apparatus 10 as described with reference to FIGS. 1 to 8.

According to such an embodiment, at least one class 104 of the one or more classes 101, 102, 103, 104 may comprise at least two class members nA, nB, wherein said one class 104 may represent a location of the movable personal appliance 11 with respect to a target surface 12, wherein a first class member nA may represent a first location zone $21_1$ of the movable personal appliance 11 with respect to the target surface 12 and wherein a second class member nB may represent a second location zone $21_2$ of the movable personal appliance 11 with respect to the target surface 12, wherein the at least one mapped motion pattern $15_1$, $15_2$, $15_3$, ..., $15_n$ may be associated with at least one of the first and the second class members nA, nB for localizing the movable personal appliance 11 within at least one of the first and the second location zones $21_1$, $21_2$ based on the motion of the movable personal appliance 11.

In other words, the one class 104 may represent a target surface 12. The class members nA, nB of said one class 104 may represent different zones $21_1$, $21_2$ of said target surface 12. Accordingly, the localization of the movable personal appliance 11 with respect to the target surface 12 may be executed by the apparatus 10 in the same or at least a similar fashion as described above with respect to the apparatus 10 with reference to FIGS. 1 to 8.

Of course, said one class 104 representing the location of the movable personal appliance 11 with respect to the target surface 12 may also be used as a class in the second step 122 of the above-described two-step procedures of FIGS. 10 and 11, e.g. after identifying a user and/or a user type.

The neural network 18 of the apparatus 100 may comprise the same or similar features as the neural network 18 of the apparatus 10 that has been described with reference to FIGS. 4 to 7. Thus, it shall be briefly referred to FIG. 7 again.

According to an embodiment, the neural network 18 may comprise at least a first and a second layer 71, 72, wherein each layer may comprise a neural unit 60, 70, wherein at a first time instant t the at least one inertial sensor data $X_t$ $17_2$ may be input into the neural unit 60 of the first layer 71, and wherein at a subsequent second time instant t+1 a second inertial sensor data $X_{t+1}$ $17_3$ and at least one output $h_t$ 46 of the previous first time instant t may be input into the neural unit 60 of the first layer 71, and/or wherein at the subsequent second time instant t+1 the at least one output $h_t$ 46 of the first time instant t may be input into the neural unit 71 of the second layer 72.

Everything that has been described above with respect to any features of the neural network 18 of the apparatus 10 as shown in FIGS. 4 to 7 also holds true for the neural network 18 of the apparatus 100 as described with reference to FIGS. 9 to 11.

Figure 12:
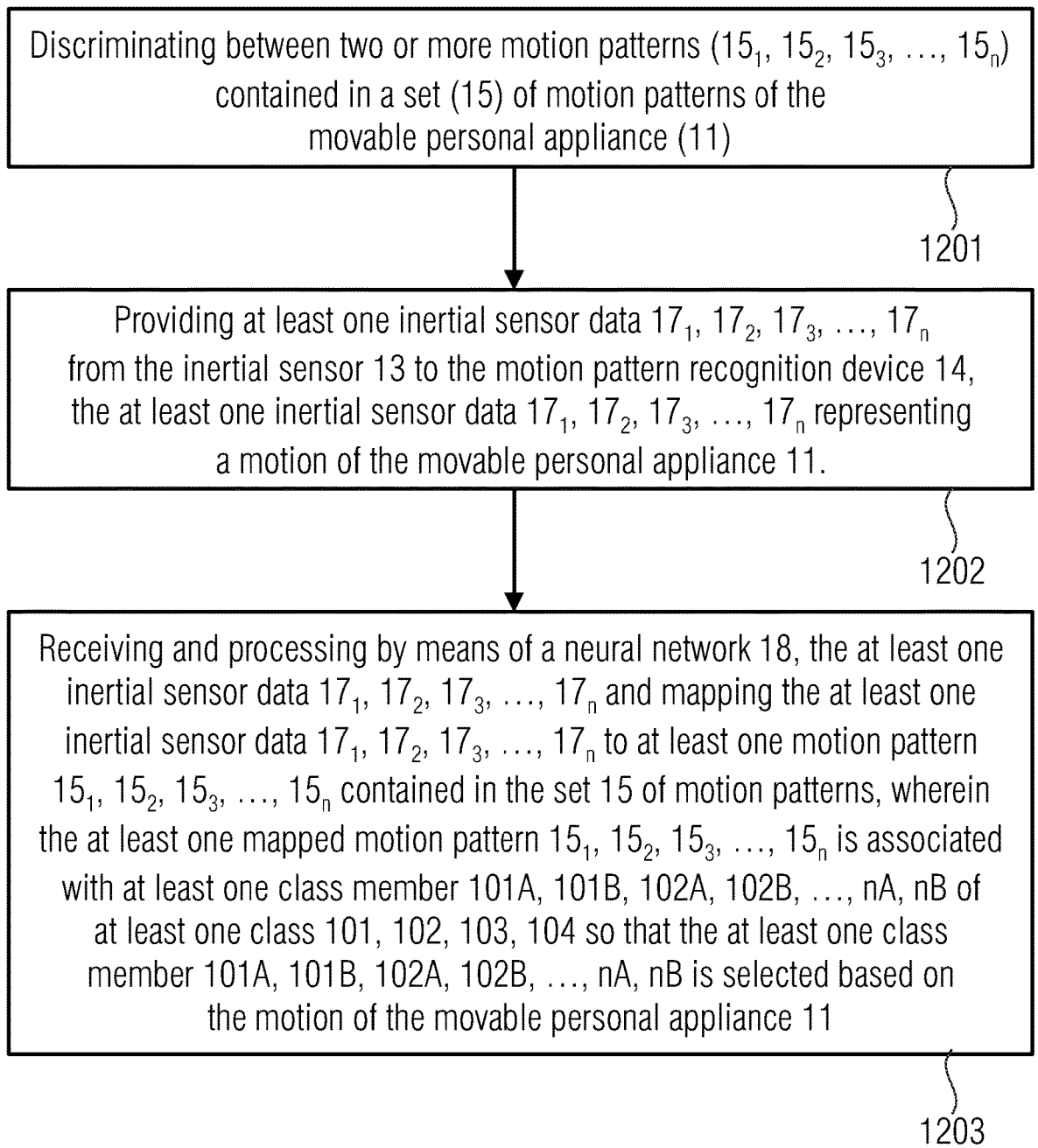
FIG. 12 shows a block diagram of an inventive method according to an embodiment.

FIG. 12 shows a block diagram of an inventive method for classifying a motion of a movable personal appliance 11 that comprises an inertial sensor 13.

In block 1201 the method comprises a step of discriminating between two or more motion patterns $15_1$, $15_2$, $15_3$, ..., $15_n$ contained in a set 15 of motion patterns of the movable personal appliance 11.

In block 1202 the method comprises a step of providing at least one inertial sensor data $17_1$, $17_2$, $17_3$, ..., $17_n$ from the inertial sensor 13 to the motion pattern recognition device 14, the at least one inertial sensor data $17_1$, $17_2$, $17_3$, ..., $17_n$ representing a motion of the movable personal appliance 11.

In Block 1203 the method comprises a step of receiving and processing, by means of a neural network 18, the at least one inertial sensor data $17_1$, $17_2$, $17_3$, ..., $17_n$ and mapping the at least one inertial sensor data $17_1$, $17_2$, $17_3$, ..., $17_n$ to at least one motion pattern $15_1$, $15_2$, $15_3$, ..., $15_n$ contained in the set 15 of motion patterns, wherein the at least one mapped motion pattern $15_1$, $15_2$, $15_3$, ..., $15_n$ is associated with at least one class member 101A, 101B, 102A, 102B, ..., nA, nB of at least one class 101, 102, 103, 104 so that the at least one class member 101A, 101B, 102A, 102B, ..., nA, nB is selected based on the motion of the movable personal appliance 11.

According to yet a further example of the inventive apparatus 10, 100 the movable treatment device 11 may be a personal appliance and the target surface 12 may be a body portion to be treated by the movable treatment device 11.

According to yet a further example of the inventive apparatus 10, 100 the movable treatment device 11 or the movable personal appliance 11 may comprise a pressure sensor for sensing a pressure applied onto a target zone by the personal appliance and/or a load sensor for sensing a motor load of a motor that may drive the personal appliance.

Respective sensor data of the pressure sensor and/or the load sensor may be fed as input into the neural unit 18, in addition or alternatively to the at least one inertial sensor data $17_1$, $17_2$, $17_3$, ... $17_n$.

According to yet a further example of the inventive apparatus 10, the apparatus 10 may comprise an output interface for outputting to a user the one or more zones $21_1$, $21_2$, $21_3$, ..., $21_n$ of the target surface 12 in which the movable treatment device 11 is located.

According to yet a further example of the inventive apparatus 100, the apparatus 100 may comprise an output interface for outputting information to a user, said information being related to the one or more classes 101, 102, 103, 104 and/or to the one or more class members 101A, 101B, ..., nA, nB of the one or more classes 101, 102, 103, 104.

In each of the herein described embodiments, sensor data $17_1$, $17_2$, $17_3$, ..., $17_n$ can be stored on the movable personal appliance or treatment device 11 and later on can be fed into the apparatus 10, 100, in a way as described above. Any post processing of this stored sensor data $17_1$, $17_2$, $17_3$, ..., $17_n$ into different zones or classes may be used to show a consumer or user on a dashboard how well and what zones they covered, what they forgot, what was in target vs out of target. This data may be shown as one usage or aggregated uses over time (i.e. show the consumer or user a simple dashboard of how they have been brushing over the week).

The invention may further comprise the following features:
- Attention mechanism (add on to the RNN);
- Prefiltering work;
- Removing head position dependency (looking at linear acc1);
- Dynamic time warping for user ID (finger print);
- Local high-freq sampling and 8 bit FFT to diff lingual and buccal (based on cheek damping of signal—this would be done by simple on device classifier followed by raw signal+device classifier into RNN;
- Not only train a position predictor, but also train a "brushing correctly vs not";
- Doing cluster analysis (have user brush 1-5 times before placing them into a bucket) to put user in a defined space that uses a custom trained RNN for that type of user.

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus. Some or all of the method steps may be executed by (or using) a hardware apparatus, like for example, a microprocessor, a programmable computer or an electronic circuit. In some embodiments, one or more of the most important method steps may be executed by such an apparatus.

Depending on certain implementation requirements, embodiments of the invention can be implemented in hardware or in software or at least partially in hardware or at least partially in software. The implementation can be performed using a digital storage medium, for example a floppy disk, a DVD, a Blu-Ray, a CD, a ROM, a PROM, an EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments according to the invention comprise a data carrier having electronically readable control signals, which are capable of cooperating with a programmable computer system, such that one of the methods described herein is performed.

Generally, embodiments of the present invention can be implemented as a computer program product with a program code, the program code being operative for performing one of the methods when the computer program product runs on a computer. The program code may for example be stored on a machine-readable carrier.

Other embodiments comprise the computer program for performing one of the methods described herein, stored on a machine-readable carrier.

In other words, an embodiment of the inventive method is, therefore, a computer program having a program code for performing one of the methods described herein, when the computer program runs on a computer.

A further embodiment of the inventive methods is, therefore, a data carrier (or a digital storage medium, or a computer-readable medium) comprising, recorded thereon, the computer program for performing one of the methods described herein. The data carrier, the digital storage medium or the recorded medium are typically tangible and/or non-transitory.

A further embodiment of the inventive method is, therefore, a data stream or a sequence of signals representing the computer program for performing one of the methods described herein. The data stream or the sequence of signals may for example be configured to be transferred via a data communication connection, for example via the Internet, via Bluetooth Low Energy (BLE), via WiFi, or via any kind of network, for instance via a meshed network.

A further embodiment comprises a processing means, for example a computer, or a programmable logic device, configured to or adapted to perform one of the methods described herein.

A further embodiment comprises a computer having installed thereon the computer program for performing one of the methods described herein.

A further embodiment according to the invention comprises an apparatus or a system configured to transfer (for example, electronically or optically) a computer program for performing one of the methods described herein to a receiver. The receiver may, for example, be a computer, a mobile device, a memory device or the like. The apparatus or system may, for example, comprise a file server for transferring the computer program to the receiver.

In some embodiments, a programmable logic device (for example a field programmable gate array) may be used to perform some or all of the functionalities of the methods described herein. In some embodiments, a field programmable gate array may cooperate with a microprocessor to perform one of the methods described herein. Generally, the methods are preferably performed by any hardware apparatus.

The apparatus described herein may be implemented using a hardware apparatus, or using a computer, or using a combination of a hardware apparatus and a computer.

The methods described herein may be performed using a hardware apparatus, or using a computer, or using a combination of a hardware apparatus and a computer.

The above-described embodiments are merely illustrative for the principles of the present invention. It is understood that modifications and variations of the arrangements and the details described herein will be apparent to others skilled in the art. It is the intent, therefore, to be limited only by the scope of the impending patent claims and not by the specific details presented by way of description and explanation of the embodiments herein.

Furthermore, the dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An apparatus (10) for performing a localization of a movable treatment device (11) relative to a target surface (12), the movable treatment device (11) comprising an inertial sensor (13) and being configured to treat the target surface (12), the apparatus (10) comprising:
   a motion pattern recognition device (14) configured to discriminate between two or more motion patterns ($15_1$, $15_2$, $15_3$, ..., $15_n$) contained in a set (15) of motion patterns of the movable treatment device (11), and
   an interface (16) for providing at least one inertial sensor data ($17_1$, $17_2$, $17_3$, ..., $17_n$) from the inertial sensor (13) to the motion pattern recognition device (14), the at least one inertial sensor data ($17_1$, $17_2$, $17_3$, ..., $17_n$) representing a movement of the movable treatment device (11),
   wherein the motion pattern recognition device (14) comprises a neural network (18) configured to receive the at least one inertial sensor data ($17_1$, $17_2$, $17_3$, ..., $17_n$) and to map the at least one inertial sensor data ($17_1$, $17_2$, $17_3$, ..., $17_n$) to at least one motion pattern ($15_1$, $15_2$, $15_3$, ..., $15_n$) contained in the set (15) of motion patterns, wherein said motion patterns ($15_1$, $15_2$, $15_3$, ..., $15_n$) are each associated ($20_1$, $20_2$, $20_3$, ..., $20_n$) with one or more different zones ($21_1$, $21_2$, $21_3$, ..., $21_n$) of the target surface (12) so that the mapping of the at least one inertial sensor data ($17_1$, $17_2$, $17_3$, ..., $17_n$) with the at least one motion pattern ($15_1$, $15_2$, $15_3$, ..., $15_n$) indicates an estimation of the location of the movable treatment device (11) with respect to the one or more zones ($21_1$, $21_2$, $21_3$, ..., $21_n$) of the target surface (12),
   wherein the neural network (18) comprises a first layer (71), wherein said first layer (71) comprises a neural unit (60), wherein at a first time instant t the at least one inertial sensor data ($17_2$) is input into the neural unit (60) of the first layer (71), and wherein at a subsequent second time instant t+1 a second inertial sensor data ($17_3$) and at least one output ht (46) of the previous first time instant t are input into the neural unit (60) of the first layer (71).

2. The apparatus (10) of claim 1, wherein the movable treatment device (11) is an oral care device and the target surface (12) is a dentition, wherein the dentition (12) is separated into different dental zones (1a-9a), and wherein the mapping of the at least one inertial sensor data ($17_1$, $17_2$, $17_3$, ..., $17_n$) with the at least one motion pattern ($15_1$, $15_2$, $15_3$, ..., $15_n$) indicates an estimation of the location of the oral care device (11) with respect to the one or more dental zones (1a-9a) of the dentition (12).

3. The apparatus (10) of claim 2, wherein the dentition (12) is separated into nine dental zones (1a-9a), wherein a first dental zone (1a) corresponds to the buccal side of the left side of the upper and lower jaw of the dentition (12), a second dental zone (2a) corresponds to the occlusal side of the left and right side of the upper jaw of the dentition (12), a third dental zone (3a) corresponds to the occlusal side of the left and right side of the lower jaw of the dentition (12), a fourth dental zone (4a) corresponds to the lingual side of the left side of the upper and lower jaw of the dentition (12), a fifth dental zone (5a) corresponds to the buccal side of the right side of the upper and lower jaw of the dentition (12), a sixth dental zone (6a) corresponds to the lingual side of the left side of the upper and lower jaw of the dentition (12), a seventh dental zone (7a) corresponds to the labial side of the upper and lower jaw of the dentition (12), an eighth dental zone (8a) corresponds to the palatal side of the upper jaw of the dentition (12), and a ninth dental zone (9a) corresponds to the oral side of the front lower jaw of the dentition (12).

4. The apparatus (10) of claim 2, wherein at least one predetermined motion pattern ($15_{NB}$) contained in the set (15) of motion patterns is associated with a zone ($21_{NB}$) outside the target surface (12), and wherein the mapping of the at least one inertial sensor data ($17_1$, $17_2$, $17_3$, ..., $17_n$) with the at least one predetermined motion pattern ($15_{NB}$) indicates that the movable treatment device (11) is located in said zone ($21_{NB}$) outside the target surface (12).

5. The apparatus (10) of claim 1, wherein the movable treatment device (11) is a personal appliance and the target surface (12) is a body portion to be treated by the movable treatment device (11).

6. The apparatus (10) of claim 1, wherein the neural network (18) is a Recurrent Neural Network—RNN.

7. The apparatus (10) of claim 1, wherein the at least one inertial sensor data ($17_1$, $17_2$, $17_3$, ..., $17_n$) comprises at least three inertial sensor data portions of the group comprising a linear velocity in x, y and z direction, an angular velocity with respect to the x, y and z axes, a linear acceleration in x, y and z direction, and an angular acceleration with respect to the x, y and z axes.

8. The apparatus (10) of claim 1, wherein an output y(t) of the neural network (18) comprises one or more probability values for the estimation of the location of the movable treatment device (11) with respect to the one or more zones ($21_1$, $21_2$, $21_3$, ..., $21_n$) of the target surface (12).

9. The apparatus (10) of claim 1, wherein the motion pattern recognition device (14) is configured to determine from the at least one inertial sensor data ($17_1$, $17_2$, $17_3$, ..., $17_n$) a mutual movement of the movable treatment device (11) and the target surface (12), and to remove the determined movement of the target surface (12) from the determined movement of the movable treatment device (11).

10. An apparatus (10) for performing a localization of a movable treatment device (11) relative to a target surface (12), the movable treatment device (11) comprising an inertial sensor (13) and being configured to treat the target surface (12), the apparatus (10) comprising:
   a motion pattern recognition device (14) configured to discriminate between two or more motion patterns ($15_1$, $15_2$, $15_3$, ..., $15_n$) contained in a set (15) of motion patterns of the movable treatment device (11), and
   an interface (16) for providing at least one inertial sensor data ($17_1$, $17_2$, $17_3$, ..., $17_n$) from the inertial sensor (13) to the motion pattern recognition device (14), the at least one inertial sensor data ($17_1$, $17_2$, $17_3$, ..., $17_n$) representing a movement of the movable treatment device (11),
   wherein the motion pattern recognition device (14) comprises a neural network (18) configured to receive the at least one inertial sensor data ($17_1$, $17_2$, $17_3$, ..., $17_n$) and to map the at least one inertial sensor data ($17_1$, $17_2$, $17_3$, ..., $17_n$) to at least one motion pattern ($15_1$, $15_2$, $15_3$, ..., $15_n$) contained in the set (15) of motion patterns, wherein said motion patterns ($15_1$, $15_2$, $15_3$, ..., $15_n$) are each associated ($20_1$, $20_2$, $20_3$, ..., $20_n$) with one or more different zones ($21_1$, $21_2$, $21_3$, ..., $21_n$) of the target surface (12) so that the mapping of the at least one inertial sensor data ($17_1$, $17_2, 17_3, \ldots, 17_n$) with the at least one motion pattern ($15_1, 15_2, 15_3, \ldots, 15_n$) indicates an estimation of the location of the movable treatment device (11) with respect to the one or more zones ($21_1, 21_2, 21_3, \ldots, 21_n$) of the target surface (12), wherein the neural network (18) comprises at least a first layer (71) and a second layer (72), wherein the first layer (71) comprises a first neural unit (60) and wherein the second layer (72) comprises a second neural unit (70), wherein at a first time instant t the at least one inertial sensor data ($17_2$) is input into the first neural unit (60) of the first layer (71), and wherein at least one output $h_t$ (46) of the first neural unit (60) is input into the second neural unit (70) of the second layer (72).

11. An apparatus (10) for performing a localization of a movable treatment device (11) relative to a target surface (12), the movable treatment device (11) comprising an inertial sensor (13) and being configured to treat the target surface (12), the apparatus (10) comprising:
  a motion pattern recognition device (14) configured to discriminate between two or more motion patterns ($15_1, 15_2, 15_3, \ldots, 15_n$) contained in a set (15) of motion patterns of the movable treatment device (11), and
  an interface (16) for providing at least one inertial sensor data ($17_1, 17_2, 17_3, \ldots, 17_n$) from the inertial sensor (13) to the motion pattern recognition device (14), the at least one inertial sensor data ($17_1, 17_2, 17_3, \ldots, 17_n$) representing a movement of the movable treatment device (11),
  wherein the motion pattern recognition device (14) comprises a neural network (18) configured to receive the at least one inertial sensor data ($17_1, 17_2, 17_3, \ldots, 17_n$) and to map the at least one inertial sensor data ($17_1, 17_2, 17_3, \ldots, 17_n$) to at least one motion pattern ($15_1, 15_2, 15_3, \ldots, 15_n$) contained in the set (15) of motion patterns, wherein said motion patterns ($15_1, 15_2, 15_3, \ldots, 15_n$) are each associated ($20_1, 20_2, 20_3, \ldots, 20_n$) with one or more different zones ($21_1, 21_2, 21_3, \ldots, 21_n$) of the target surface (12) so that the mapping of the at least one inertial sensor data ($17_1, 17_2, 17_3, \ldots, 17_n$) with the at least one motion pattern ($15_1, 15_2, 15_3, \ldots, 15_n$) indicates an estimation of the location of the movable treatment device (11) with respect to the one or more zones ($21_1, 21_2, 21_3, \ldots, 21_n$) of the target surface (12),
  wherein the neural network (18) comprises at least a first layer (71) and a second layer (72), wherein the first layer (71) comprises a first neural unit (60) and wherein the second layer (72) comprises a second neural unit (70), wherein at a first time instant t the at least one inertial sensor data (17$_2$) is input into the first neural unit (60) of the first layer (71), and wherein at least one output $h_t$ (46) of the first neural unit (60) is input into the neural unit (70) of the second layer (72), and wherein at a subsequent second time instant t+1 a second inertial sensor data (17$_3$) and at least one output $h_t$ (46) of the first neural unit (60) at the first time instant t is input into the first neural unit (60) at the subsequent second time instant t+1.

12. An apparatus (10) for performing a localization of a movable treatment device (11) relative to a target surface (12), the movable treatment device (11) comprising an inertial sensor (13) and being configured to treat the target surface (12), the apparatus (10) comprising:
  a motion pattern recognition device (14) configured to discriminate between two or more motion patterns ($15_1, 15_2, 15_3, \ldots, 15_n$) contained in a set (15) of motion patterns of the movable treatment device (11), and
  an interface (16) for providing at least one inertial sensor data ($17_1, 17_2, 17_3, \ldots, 17_n$) from the inertial sensor (13) to the motion pattern recognition device (14), the at least one inertial sensor data ($17_1, 17_2, 17_3, \ldots, 17_n$) representing a movement of the movable treatment device (11),
  wherein the motion pattern recognition device (14) comprises a neural network (18) configured to receive the at least one inertial sensor data ($17_1, 17_2, 17_3, \ldots, 17_n$) and to map the at least one inertial sensor data ($17_1, 17_2, 17_3, \ldots, 17_n$) to at least one motion pattern ($15_1, 15_2, 15_3, \ldots, 15_n$) contained in the set (15) of motion patterns, wherein said motion patterns ($15_1, 15_2, 15_3, \ldots, 15_n$) are each associated ($20_1, 20_2, 20_3, \ldots, 20_n$) with one or more different zones ($21_1, 21_2, 21_3, \ldots, 21_n$) of the target surface (12) so that the mapping of the at least one inertial sensor data ($17_1, 17_2, 17_3, \ldots, 17_n$) with the at least one motion pattern ($15_1, 15_2, 15_3, \ldots, 15_n$) indicates an estimation of the location of the movable treatment device (11) with respect to the one or more zones ($21_1, 21_2, 21_3, \ldots, 21_n$) of the target surface (12),
  wherein the at least one inertial sensor data ($17_1, 17_2, 17_3, \ldots, 17_n$) comprises one or more inertial sensor data portions, and wherein an input to the neural unit (60) at a first time instant t is a respective inertial sensor data ($17_1, 17_2, 17_3, \ldots, 17_n$) comprising the one or more inertial sensor data portions retrieved during said first time instant t.

\* \* \* \* \*